United States Patent
Henniges et al.

(10) Patent No.: US 7,153,287 B2
(45) Date of Patent: Dec. 26, 2006

(54) SURGICAL/MEDICAL IRRIGATOR WITH REMOVABLE SPLASH SHIELD

(75) Inventors: Bruce D. Henniges, Kalamazoo, MI (US); David A. Burke, Portage, MI (US)

(73) Assignee: Stryker Corporation, Kalamazoo, MI (US)

( * ) Notice: Subject to any disclaimer, the term of this patent is extended or adjusted under 35 U.S.C. 154(b) by 704 days.

(21) Appl. No.: 10/264,693

(22) Filed: Oct. 4, 2002

(65) Prior Publication Data

US 2003/0036723 A1 Feb. 20, 2003

Related U.S. Application Data

(62) Division of application No. 10/046,518, filed on Jan. 14, 2002, now Pat. No. 6,471,668, which is a division of application No. 09/704,835, filed on Oct. 31, 2001, now Pat. No. 6,352,527, which is a division of application No. 09/425,820, filed on Oct. 22, 1999, now Pat. No. 6,179,807, which is a division of application No. 08/915,431, filed on Aug. 20, 1997, now Pat. No. 6,099,494.

(51) Int. Cl.
*A61M 1/00* (2006.01)

(52) U.S. Cl. ............... 604/35; 604/39; 604/131

(58) Field of Classification Search ............ 604/19, 604/21, 27, 30–35, 39, 40, 43, 131, 151, 604/153, 902, 540, 541, 543, 317, 187, 319–321, 604/119; 323/911; 128/919; 239/102.1; 606/167, 185, 172
See application file for complete search history.

(56) References Cited

U.S. PATENT DOCUMENTS

| | | | |
|---|---|---|---|
| 3,749,090 | A | 7/1973 | Stewart |
| 4,489,750 | A | 12/1984 | Nehring |
| 4,493,694 | A | 1/1985 | Wuchinich |
| 4,519,385 | A | 5/1985 | Atkinson et al. |
| D281,535 | S | 11/1985 | Atkinson et al. |

(Continued)

OTHER PUBLICATIONS

Zimmer, *The Zimmer Var-A-Pulse* Wound Debridement System, Dec. 1996, 2 pgs.

(Continued)

*Primary Examiner*—Cris L. Rodriguez
(74) *Attorney, Agent, or Firm*—Flynn, Thiel, Boutell & Tanis, P.C.

(57) ABSTRACT

A surgical/medical irrigator with a handpiece in which there is a pump from which irrigating fluid is discharged. The irrigating fluid is discharged from a discharge tube attached to the handpiece. Irrigating fluid is removed from the site to which it is applied through a suction tube also attached to the handpiece. A splash shield is removably attached to the ends of the discharge and suction tubes to limit fluid discharge. The splash shield is formed with a discharge chamber into which the fluid from the discharge chamber is discharged. The splash shield has a bore that leads from the discharge chamber to the suction tube through which fluid is drawn away from the discharge chamber. Seals between the discharge and suction tubes and the splash shield prevent fluid flow between the tubes and the splash shield.

39 Claims, 16 Drawing Sheets

U.S. PATENT DOCUMENTS

| | | | |
|---|---|---|---|
| 4,555,645 A | 11/1985 | Atkinson | |
| 4,561,431 A | 12/1985 | Atkinson | |
| 4,583,531 A | 4/1986 | Mattchen | |
| 4,635,621 A | 1/1987 | Atkinson | |
| 4,662,829 A | 5/1987 | Nehring | |
| 4,665,558 A | 5/1987 | Burke | |
| 4,692,140 A | 9/1987 | Olson | |
| 4,741,678 A | 5/1988 | Nehring | |
| 4,776,840 A | 10/1988 | Freitas et al. | |
| 4,941,872 A * | 7/1990 | Felix et al. | 604/27 |
| 4,957,483 A | 9/1990 | Gonser et al. | |
| 5,037,431 A | 8/1991 | Summers et al. | |
| 5,046,486 A * | 9/1991 | Grulke et al. | 601/161 |
| 5,147,292 A * | 9/1992 | Kullas et al. | 604/34 |
| 5,269,750 A | 12/1993 | Grulke et al. | |
| D356,146 S | 3/1995 | Palmaymesa | |
| 5,429,596 A * | 7/1995 | Arias et al. | 604/21 |
| 5,460,604 A * | 10/1995 | Arnett et al. | 604/35 |
| 5,464,390 A * | 11/1995 | Arnett et al. | 604/35 |
| 5,470,305 A * | 11/1995 | Arnett et al. | 601/161 |
| 5,484,402 A | 1/1996 | Saravia et al. | |
| 5,609,573 A * | 3/1997 | Sandock | 604/22 |
| 5,647,852 A * | 7/1997 | Atkinson | 604/151 |
| 5,735,833 A * | 4/1998 | Olson | 604/289 |
| 5,738,648 A * | 4/1998 | Lands et al. | 604/35 |
| 5,746,721 A * | 5/1998 | Pasch et al. | 604/153 |
| 5,792,098 A * | 8/1998 | Felix et al. | 604/27 |
| 5,827,218 A | 10/1998 | Nguyen et al. | |
| 5,941,851 A * | 8/1999 | Coffey et al. | 604/131 |
| 6,059,792 A | 5/2000 | Josephberg | |
| 6,106,494 A | 8/2000 | Saravia et al. | |
| 6,156,004 A * | 12/2000 | Tremaine et al. | 604/27 |
| 6,200,292 B1 * | 3/2001 | French et al. | 604/131 |
| 6,213,970 B1 | 4/2001 | Nelson et al. | 604/35 |
| 6,364,853 B1 | 4/2002 | French et al. | 604/35 |
| 6,394,996 B1 * | 5/2002 | Lawrence et al. | 604/540 |
| 6,485,452 B1 | 11/2002 | French et al. | |

OTHER PUBLICATIONS

Zimmer, *It's a Matter of Time* The Pulsavac System, Dec. 1994, 6 pgs.

Zimmer, *Pulsavac* Wound Debridement System for Power and Control, Dec. 1996, 8 pgs.

Davol, *To Pulsed Lavage, The Choice Is Remarkably Simple*, Jan. 1995, 4 pgs.

Davol, *Performance Irrigation™ Systems*, Pulsed Lavage for Wound Management, Dec. 1995, 2 pgs.

Davol, *To Pulsed Lavage, The Choice is Simple*, Sep. 1994, 3 pgs.

Maxim Max712/max713 Battery Fast Charge Controllers, datasheet, Data Sheet No. 19-0100, http://dbserve.maxim-ic.com, Jan. 1997 2 pgs.

Stryker Instruments, High Flow Trauma Tip Assembly and Part Diagrams, Dec. 1993.

* cited by examiner

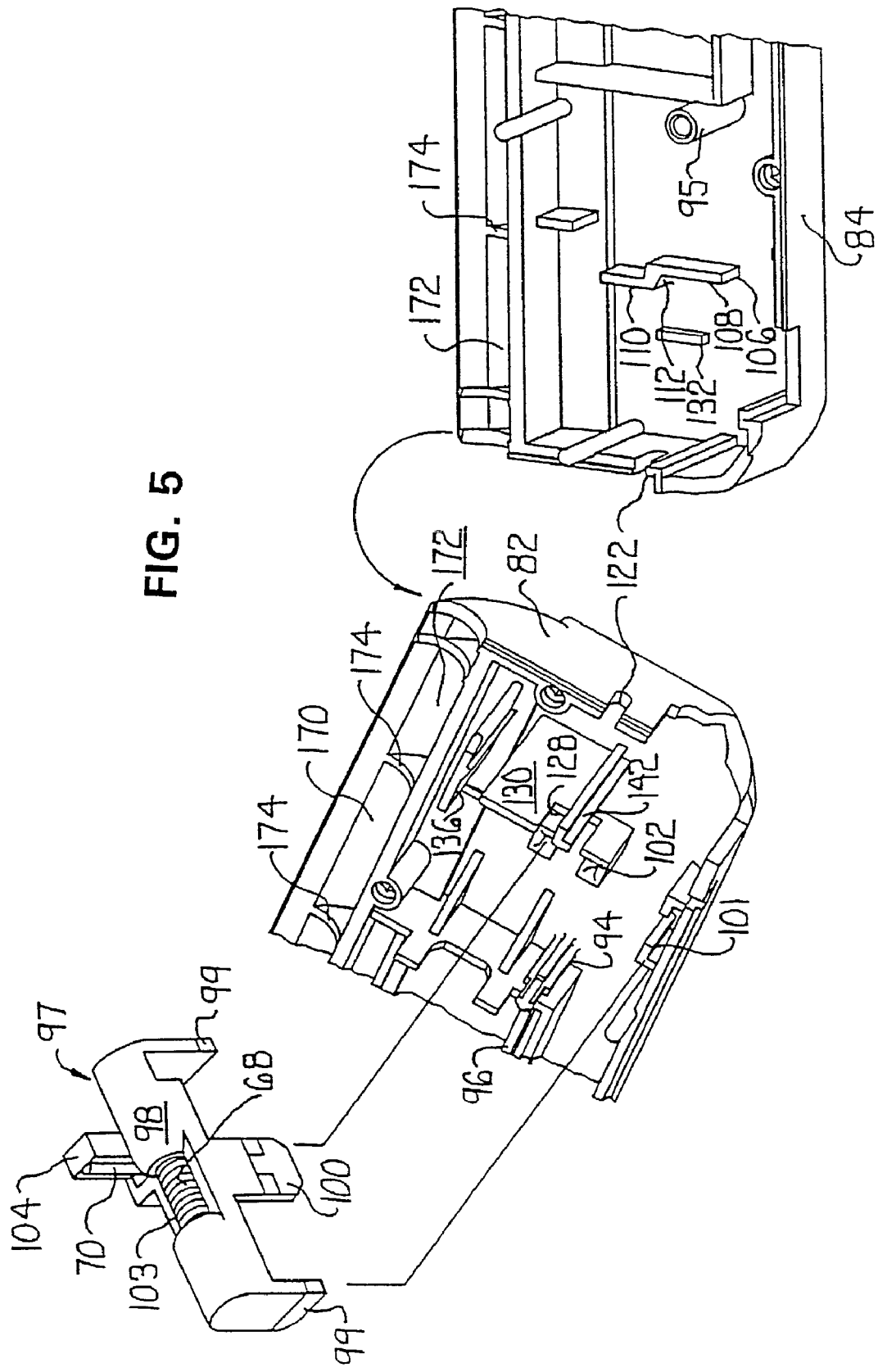

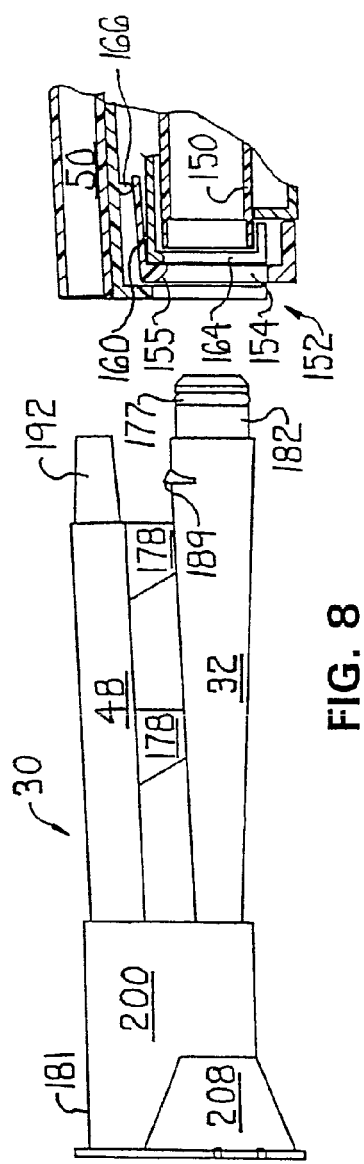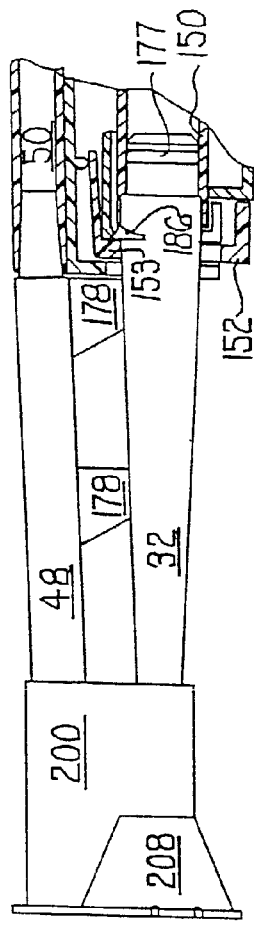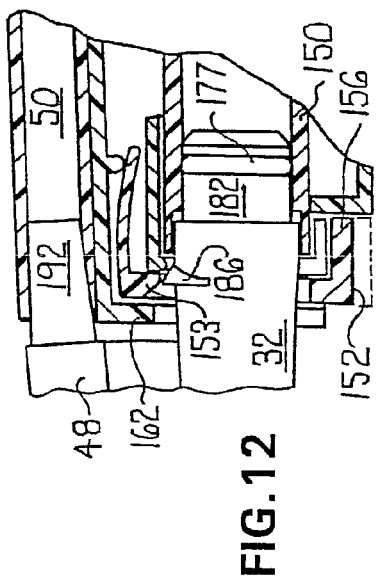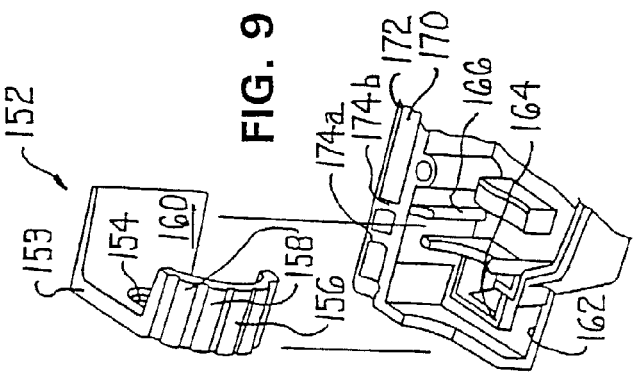

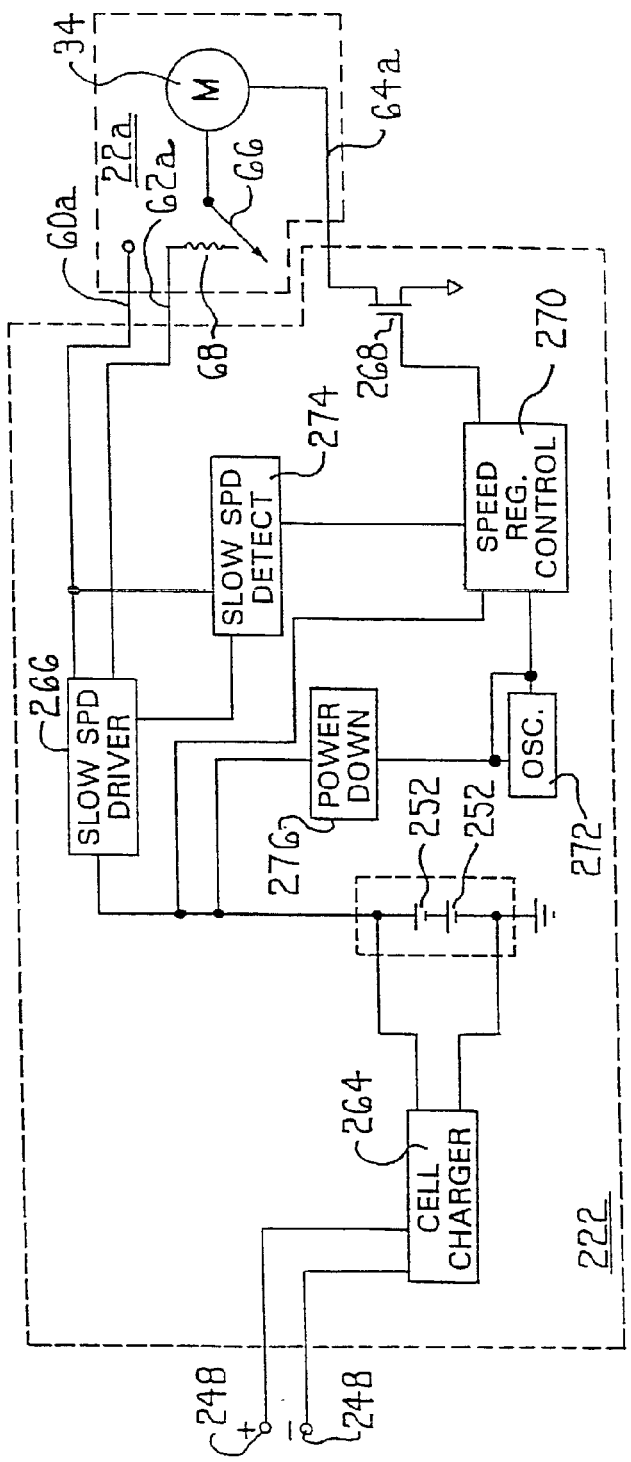

SURGICAL/MEDICAL IRRIGATOR WITH REMOVABLE SPLASH SHIELD

RELATIONSHIP TO EARLIER APPLICATIONS

This application is a divisional of U.S. patent application Ser. No. 10/046,518 filed Jan. 14, 2002, now U.S. Pat. No. 6,471,668, which is a divisional of U.S. patent application Ser. No. 09/704,835, filed Oct. 31, 2001, now U.S. Pat. No. 6,352,527, which is a divisional of U.S. patent application Ser. No. 09/425,820, filed Oct. 22, 1999, now U.S. Pat. No. 6,179,807, which is a divisional of U.S. patent application Ser. No. 08/915,431, filed Aug. 20, 1997, now U.S. Pat. No. 6,099,494. The above patents and pending application are incorporated by reference into this application.

FIELD OF THE INVENTION

This invention relates generally to an irrigator useful for surgical and medical procedures and, more particularly, to an irrigation handpiece with a removable splash shield.

BACKGROUND OF THE INVENTION

In many surgical and medical procedures, an irrigator is employed to deliver pulses of fluid to a particular location on or in the body of a person receiving medical attention. For example, during orthopedic surgery, an irrigator may be employed to deliver pressurized pulses of water or saline solution to an exposed surface of the bone in order to clean the bone. There are also some non-surgical procedures performed which likewise make it desirable to apply pulses of water to a specific site on an individual's skin. Thus, if an individual is suffering from some type of bed sore or some other type of skin wound, it is a common practice to use an irrigator to clean the wound prior to applying a dressing to the wound.

A common type of medical/surgical irrigator includes a handpiece to which a tip assembly is selectively attached. Often, inside the handpiece is a small pump that periodically delivers a quantity of pressurized fluid. Alternatively, the pressurized fluid is delivered to the handpiece from an external pump. The fluid is discharged through a discharge tube integral with the tip assembly to the selected site on or in the patient. These irrigators deliver fluid in pressurized pulses for two reasons. One reason is that fluid pulses quickly strike the site to which they are applied and leave the site; this action serves to foster the desirable removal of debris from the site. Secondly, the discrete fluid pulses do not obstruct the view of the site as much as it can be obstructed when exposed to a continuous flow of pressurized fluid.

Most irrigator handpieces, in addition to having a conduit through which the sterile fluid is discharged, have a conduit through which the discharged fluid is removed from the site to which it is applied. Typically, the fluid is initially withdrawn from the site through a suction tube, also part of the tip assembly. The fluid, as well as any debris in the fluid stream, then flow through a conduit integral with the handpiece. The handpiece suction conduit is connected to a second suction tube that is connected to a suction system separate from the irrigator. Thus, given their ability to essentially simultaneously clean a site on a patient and remove the debris generated by the cleaning process, it should be readily apparent why irrigators have become useful tools for facilitating many medical and surgical procedures.

There are, however, some disadvantages associated with current surgical irrigators. One particular disadvantage associated with some known irrigators is how the tip assembly is connected to the handpiece. When these components are coupled together there should be two leakproof seals: a first seal between the handpiece and the discharge tube through which the irrigating fluid is discharged; and a second seal between the suction tube and the complementary handpiece conduit. Some tip assemblies sometimes do not properly mate with their complementary handpieces; this results in leakage. Leakage around a tip assembly suction tube-handpiece joint is especially prone to occur when the tip assembly is exposed to side loading. This side loading occurs when the tip assembly is pressed against tissue and flexes relative to the handpiece.

Still another problem associated with some irrigators is that the suction conduits integral to the handpieces occasionally clog. This clogging occurs because the material drawn away from the site to which the irrigator is applied is often in solid or semi-sold form. Sometimes, especially if this material is relatively large in size, the material will clog the suction conduit in the handpiece so as to significantly reduce the utility of the irrigator.

Moreover, it is desirable to provide medical personnel with some ability to control the rate at which irrigation fluid is discharged from the handpiece. Some handpieces are provided with stepped switches that are incrementally set in order to establish the voltage of the power signal applied to the motor so as to, in turn, set pump speed. One disadvantage of some known handpieces is that these switches are located in positions wherein, with a single hand, it is difficult, if not impossible, to both direct the handpiece and regulate the discharge of irrigating fluid.

Moreover, it also desirable to provide some means for controlling the pattern of the irrigating fluid discharged from the irrigator. To date, one of the more common practices is to simply provide the personnel using the irrigator with a number of different tip assemblies, each with its own nozzle that causes the irrigating fluid to be discharged in a specific spray pattern. A disadvantage of this practice is that it increases the number of different tips that a medical facility is required to keep in inventory. Still another disadvantage of this practice is that if, during a procedure, a change in fluid flow patterns is desired, the medical personnel must spend time switching tips.

Also, while it is common practice to provide handpieces with use-once, disposable battery packs, there are some circumstances when it may be more economical to provide a rechargeable power pack for repeatedly energizing different handpieces.

SUMMARY OF THE INVENTION

This invention relates to a new irrigator for medical and surgical procedures with a tip assembly that readily seals to the complementary handpiece, and a handpiece with a suction conduit that is not prone to clogging and a switch that allows easy control of pump speed. This invention also relates to a tip assembly for a handpiece with a nozzle that allows one to set the spray pattern of the fluid delivered by the nozzle. This invention further relates to a new irrigator with a rechargeable power pack that can provide drive signals of different potentials to the handpiece and that, even after being after discharged numerous times, can be fully recharged.

BRIEF DESCRIPTION OF THE DRAWINGS

This invention is defined with particularity in the appended claims. The advantages of the invention may be better understood by referring to the following detailed description, in which:

FIG. 5 is an exploded view of some of the components internal to the handpiece that regulate the speed of the pump;

FIG. 8 is a side, partial cross-sectional view depicting how the tip assembly is inserted in the handpiece;

FIG. 9 is a perspective view of the tip lock internal to the handpiece;

FIG. 11 is a partial cross sectional view illustrating how the tip assembly is locked into the front end of the handpiece;

FIG. 12 is a side, partial cross-sectional view depicting how the tip lock depressed to allow the removal of the tip assembly from the handpiece;

FIG. 16 is a block diagram of the electronic circuitry internal to the battery pack for both controlling the charging of the cells therein and their discharge by the handpiece;

FIG. 17 is an assembly drawing illustrating how

DETAILED DESCRIPTION

Figure 1:
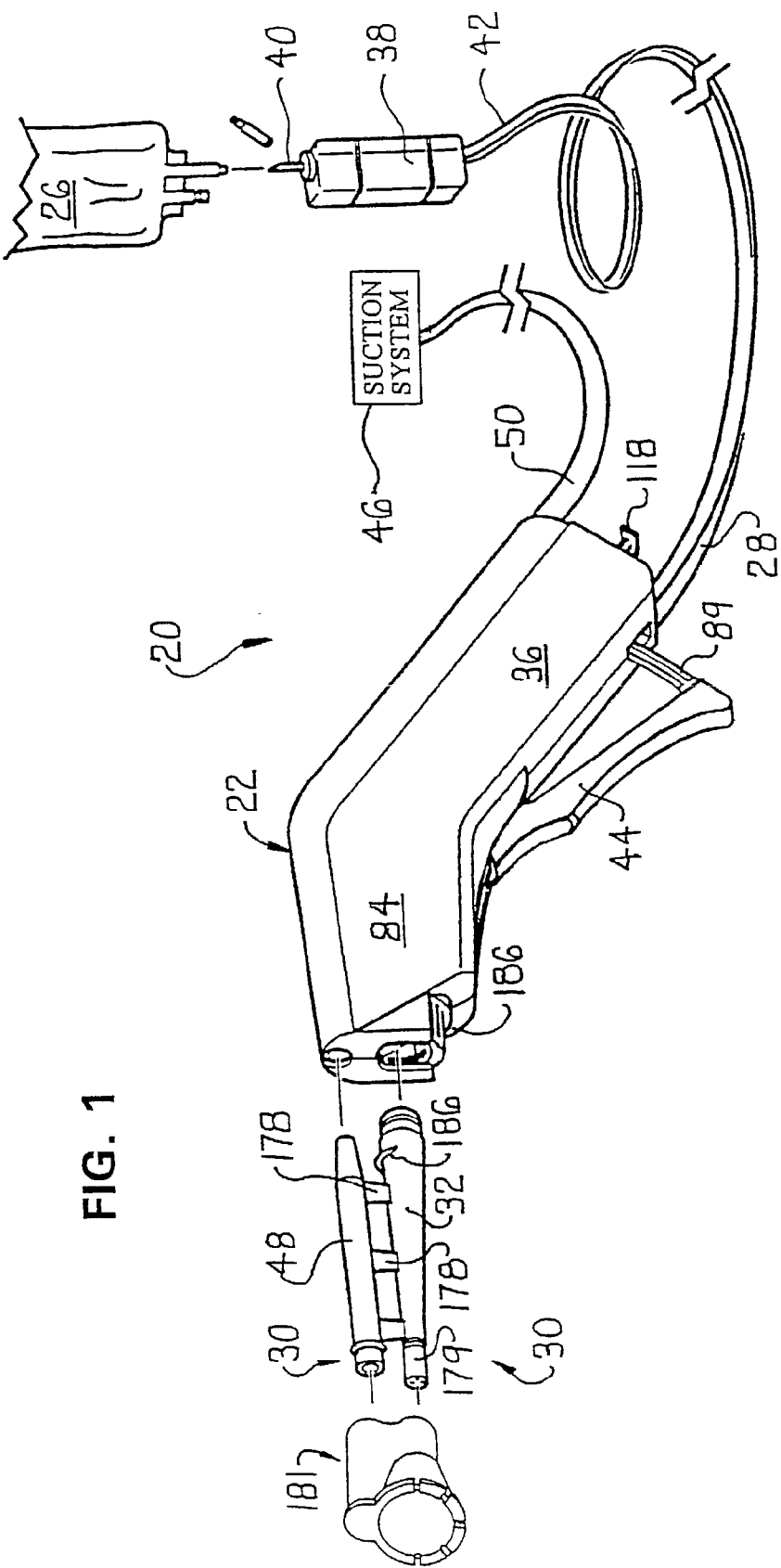
FIG. 1 depicts the basic components of an irrigator of this invention.
Figure 2:
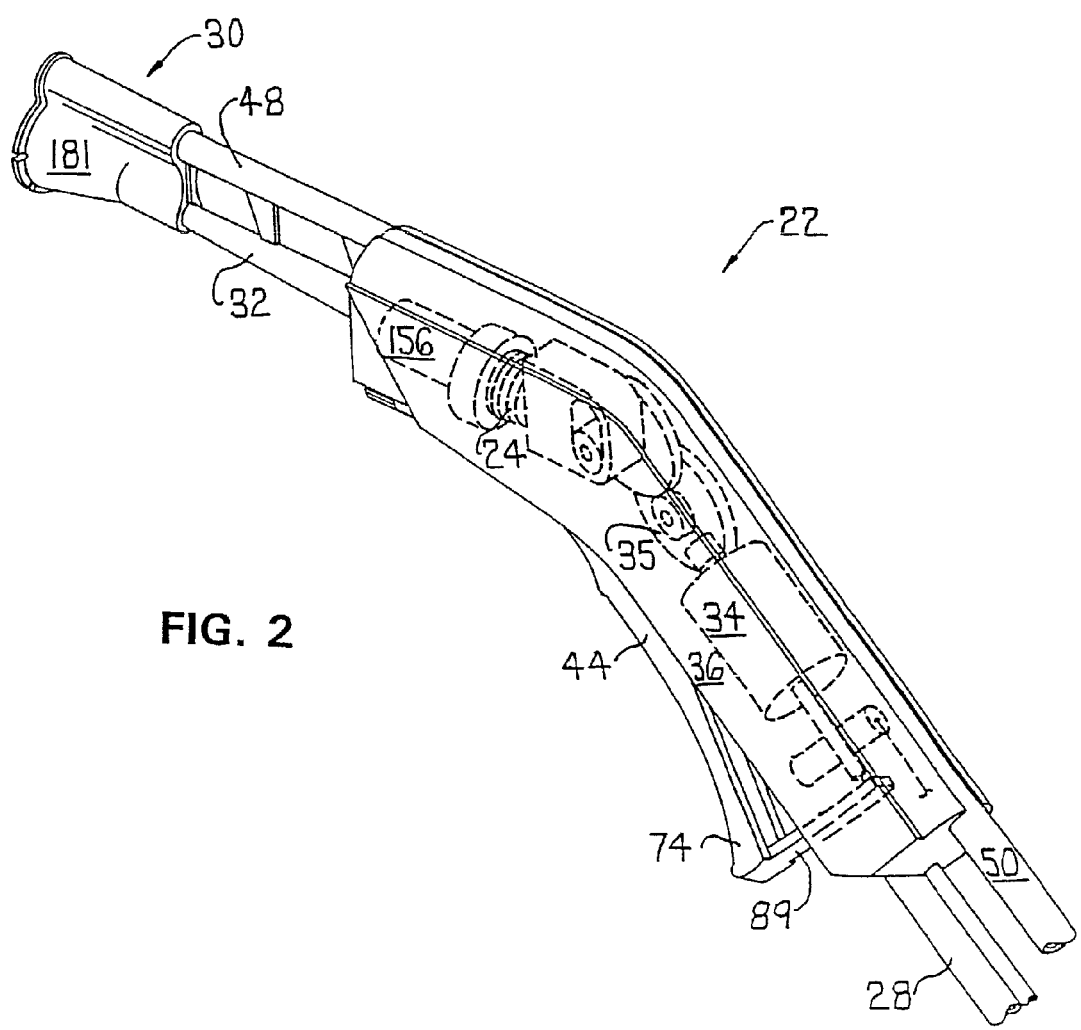
FIG. 2 is a view of the handpiece of the irrigator that illustrates the basic components internal to the handpiece.

FIGS. 1 and 2 illustrate a basic irrigator 20 of this invention. Irrigator 20 includes a handpiece 22 with a pump 24 that discharges pulses of fluid to a specific site on or in the body of the patient. The fluid is stored in a bag 26 and is gravity fed or suction drawn into the handpiece through a supply tube 28. The fluid is discharged from the front end of the handpiece 22 through a removable tip assembly 30. More particularly, tip assembly 30 has a discharge tube 32 in fluid communication with the pump 24 that is directed to the desired discharge site. The mechanical force for actuating the pump 24 comes from a motor 34. Mechanically, the rotational force developed by motor 34 is provided to pump 24 through a gear train 35. The motor 34 is mounted a lower section of the handpiece 22 hereinafter referred to as the handgrip 36.

Current for energizing the motor 34 is supplied by a battery pack 38. In the depicted version of the invention, battery pack 38 is provided with a spike 40, for establishing a fluid communication path to the bag 26. The end of supply tube 28 is disposed in battery pack 38 and is connected to the base end of the spike 40. A power cord 42 extends between the battery pack 38 and the handpiece 22 for supplying the energization current to the handpiece. The power cord 42 is shown as being adhesively secured to the outside of supply tube 28. A lever-like trigger 44 attached to the undersurface of the handgrip 36 is depressed to control the on/off state of the motor 34 and motor speed.

Irrigator 20 also presents a suction head to the discharge site so that the discharged fluid and any debris therein can be removed. The force for this suction head comes from a suction system 46 separate from the irrigator 20 and not part of this invention. The suction head is presented to the discharge site through the open end of a rigid suction tube 48 integral with tip assembly 30. Suction tube 48 is placed in fluid communication with suction system 46 through a flexible drain tube 50 that is mounted in the handpiece 22 and extends from the handpiece as a single tube so that it can be coupled to an inlet port, (not illustrated,) integral with the suction system 46.

Figure 4:
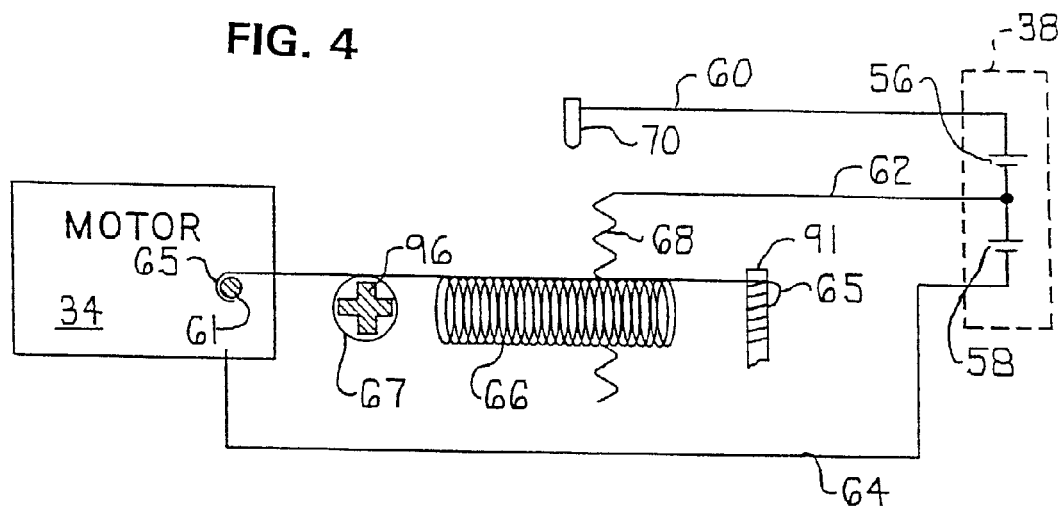
FIG. 4 is a schematic and diagrammatic illustration of the components of the irrigator that regulate the on/off state of the irrigator as well as the flow and the rate at which fluid is discharged from the irrigator.

The control of the drive signal applied to motor 34 to regulate both the on/off state of the irrigator and the rate of fluid discharge is now explained by initial reference to FIG. 4. It should be understood that internal to the battery pack 38 are two series connected cells 56 and 58. In some preferred versions of the invention, each cell 56 and 58 actually consists of four series-connected AA batteries. A circuit for supplying the energization current to the motor 34 is established by one of two power conductors 60 or 62 and a ground conductor 64 connected to the negative terminal of cell 58. Power conductor 60 is shown as being connected to the positive terminal of cell 56. Consequently, the potential across conductors 60 and 64 is the full potential developed across cells 56 and 58. Power conductor 62 is connected to the junction of cells 56 and 58; the potential across conductors 62 and 64 is just the potential developed by cell 58. Conductors 60, 62 and 64 are the conductors internal to power cord 42.

A movable spring 66 serves as the wiper that ties either conductor 60 or 62 to motor 34 to regulate the application of the energization voltage to the motor. One end of spring 66 is connected to a terminal 61 internal to motor 34 to which the positive potential is applied. Spring 66 has a first position wherein it is not connected to either conductor 60 or 62; this is the off position for the irrigator 20. When actuation of the irrigator 20 is desired, spring 66 is moved to a second position in which it is contact with the resistive wire of a wire-wound resistor 68 that is series-connected to conductor 62. In one version of the invention, resistor 68 is a 3-Ohm resistor. Resistor 68 serves as a variable load to regulate the fraction of the potential developed by cell 58 that is applied to the motor 34. When spring 66 is positioned across the full length of the resistor 68, there is the largest voltage drop across the resistor 68. Therefore, a relatively small voltage is applied to the motor 34. The motor 34 and, in turn, pump 24, operate at a relatively slow speed so as to result in the relatively slow discharge of fluid by the irrigator. When faster operation of the irrigator 20 is desired, spring 66 is repositioned along the length of resistor 68 to reduce the voltage drop across the resistor and increase the voltage applied to the motor 34.

When operation of the irrigator 20 at still higher speed is desired, spring 66 is reset to a third position wherein it is spaced from resistor 68 and abuts a fixed contact 70. Contact 70 is connected to the end of conductor 60. Consequently, when spring 66 abuts contact 70, the full potential developed across cells 56 and 58, a high speed drive signal, is applied to motor 34 so as to result in the highest speed operation of the irrigator 20.

Spring 66 is from a conductive material such as plated beryllium copper. The position of spring 66 is set by the selective movement of trigger 44, now discussed by reference to FIGS. 5 and 6A. More particularly, trigger 44 is shaped to have an elongated body 74 located along the lower, downward facing surface of handgrip 36. A finger 76 extends forward from the front end of trigger body 74. Opposed pins 78, (one shown,) extend laterally away from the sides of finger 76 seat in openings, (not depicted) formed in webs 75 integral with the right and left shells 82 and 84, respectively that form the body of handpiece 22. Pins 78 thus pivotally secure trigger 44 to the handpiece 22. A coil spring 86 located between a portion of the body 74 adjacent finger 76 and the opposed surface of the handpiece 22 normally biases trigger 44 so that its body 74 is positioned away from the adjacent lower surface of handgrip 36. When trigger 44 is so positioned, spring 66 is spaced from both resistor 68 and contact 70 so as to place the irrigator 20 in the off state.

Trigger 44 is further formed to have a single leg 89 that extends from the end of the main body 74 distal from finger 76 into the handpiece 22. Shells 82 and 84 are formed to define a slot 90 spaced forward of the rear ends of the handpiece through which leg 89 extends. In the illustrated version of the invention, leg 89 has an arcuate profile centered around the axis of pins 78. A foot 92 is attached to the end of leg 89 seated inside handpiece 22. Foot 92 is greater in width than leg 89.

Returning to FIG. 4 it can be seen that the opposed ends of spring 66 are provided with hooks 65 to facilitate the securement of the spring to the motor 34. Spring 66 is formed with a loop 67 that extends around a post 93 adjacent motor 34 to foot 92 of the trigger 44. Post 93 is actually formed from a first, male post 94 integral with right shell 82 and a female post 95 integral with left shell 84. Loop 67 is fitted over a reduced diameter boss 96 integral with male post 94 that seats in female post 95. The hook 65 integral with spring 66 adjacent loop 67 is secured to the terminal 61 internal to motor 34. The opposed hook 65 is fitted around slots 91, (one slot illustrated,) formed in foot 92 of the trigger 44. When the spring 66 is so positioned, it extends across a non-conductive resistor support 97 secured inside the right shell 82, best seen in FIGS. 5 and 6A. Resistor support 97 has an elongated sleeve-like main casing 98 in which resistor 68 is seated. Tabs 99 extend perpendicular away from the longitudinal axis of main casing 98 at the ends of the casing. A third tab 100 extends from the center of main casing towards the right shell 82. Lower tab 99 and center-located tab 100 seat in complementary sockets 101 and 102, respectively, formed in right shell 82 to hold resistor support 97 in position. The upper tab 99 simply abuts the inside wall of right shell 82 to provide mechanical support for the resistor support 97.

Main casing 98 is formed with a window 103 that exposes the wire coil of resistor 68. Resistor support 97 further includes a three-sided mounting bracket 104, which is integral with main casing 98. Mounting bracket 104 is shaped to hold fixed contact 70, which is shaped as U-shaped piece of conductive metal that is compression-secured in the mounting bracket.

Figure 6A:
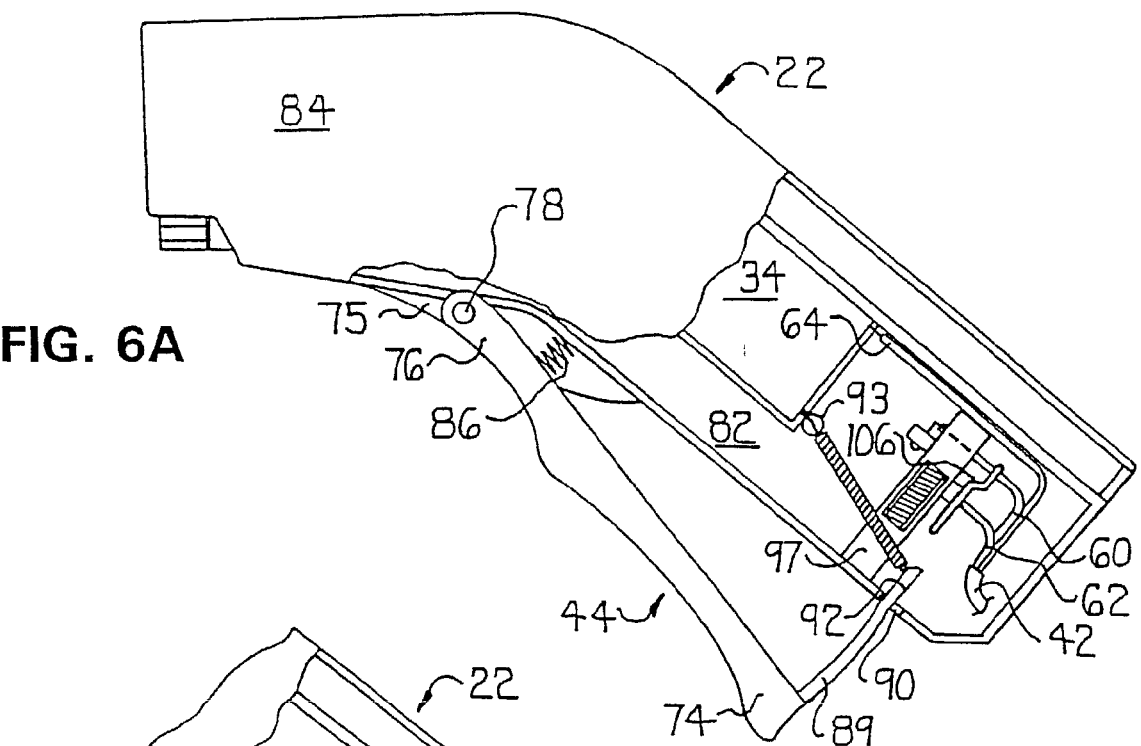
FIGS. 6A, 6B and 6C are side views illustrating the different positions of the components that regulate pump speed, depicting, respectively, their position when the irrigator is off, operated at low speed, and operated at high speed.

The position of spring 66 relative to resistor support 97 is a function of the extent to which trigger 44 is depressed. When trigger 44 is not depressed, spring 66 is located against the lower portion of the main casing 98 so as to be spaced away from both window 103 and fixed contact 70 as seen in FIG. 6A. This is the position of the spring 66 when irrigator 20 is in the off state. When low speed operation of the irrigator 20 is desired, trigger 44 is partially depressed to position spring 66 across window 103, depicted by FIG. 6B. When the spring 66 is so positioned, it abuts resistor 68 so as to allow a low voltage drive signal to be applied to motor 34. By controlling the depression of the trigger 44, the extent to which resistor 68 is placed in series with conductor 62 is controlled. This positioning allows the low speed discharge of the irrigator 20 to be selectively set over a range of operating speeds.

Figure 6B:
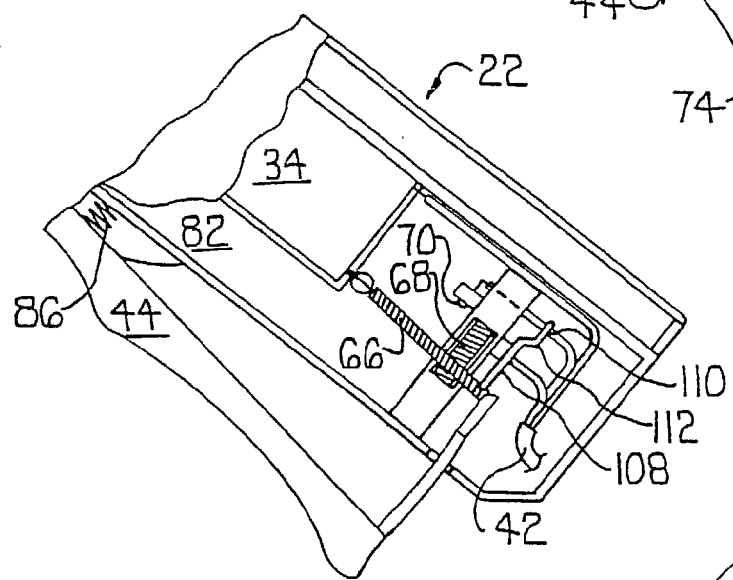
Figure 6C:
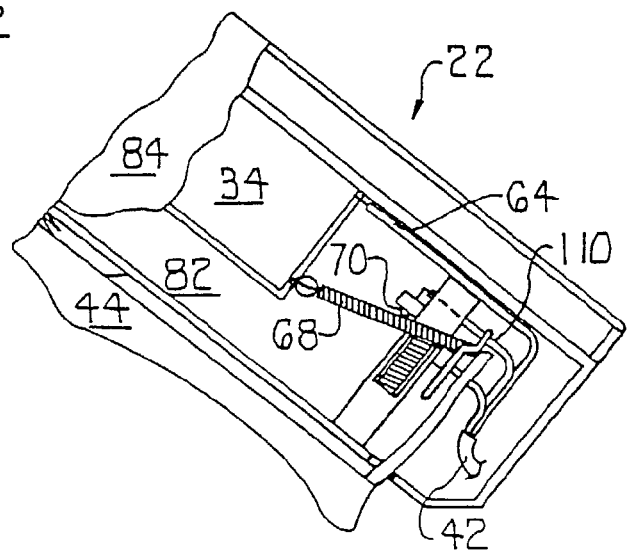

When operation of the irrigator at high speed is desired, trigger 44 is fully depressed. The complete depression of the trigger 44 pivots spring 66 away from resistor 68 and against fixed contact 70, as seen by FIG. 6C. Once the spring 66 and contact 70 abut, the full potential across cells 56 and 58 is applied to the motor 34 so as to cause the irrigator 20 to run at its highest speed.

It will further be observed from FIGS. 5 and 6A that left shell 84 is formed with a stepped rib 106 that projects into a space inside the handpiece 22 adjacent the foot 92 of trigger 44. More particularly, rib 106 extends generally perpendicularly relative to the longitudinal axis of the handgrip 36 portion of handpiece 22. Rib 106 is shaped to have a first, lower portion 108 and a second, upper portion 110 located slightly forward of lower portion 108. An angled step 112 in rib 106 serves as the transition section between the lower and upper sections 108 and 110, respectively.

When trigger 44 is depressed to operate the irrigator 20, the forward facing surface of foot 92 presses against the rearward facing surface of rib 106. When the trigger 44 is initially depressed, operated in the low speed state, foot 92 rides against the lower portion 108 of rib 106 as seen in FIG. 6B. Further depression of trigger 44 results in foot 92 seating in the space defined by step 112. If higher speed operation of irrigator 20 is desired, further depression of trigger 44 forces foot 92 out of step 112 and against the surface of upper section 110 of the rib 106. This movement of the trigger causes spring 66 to abut contact 70.

The seating of the foot 92 of trigger 44 against step 112 performs two functions. First, it holds the trigger 44 so that spring 66 is positioned so that there is a minimum voltage drop across resistor 68 and the spring will be spaced away from fixed contact 70. Thus, the trigger 44 and spring 66 are set to cause the highest possible low speed drive signal to be applied to the motor 34. Secondly, the seating of trigger 44 provides a tactile indication to the person using the irrigator 20 that continued depression of the trigger 44 will cause the irrigator to transition from the low speed operating state to the high speed operating state.

Figure 7:
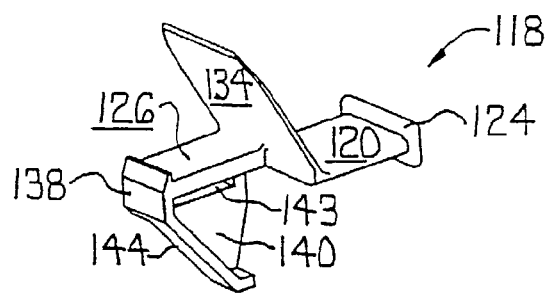
FIG. 7 illustrates the trigger lock employed to lock the irrigator into its high speed operating state.
Figure 7A:
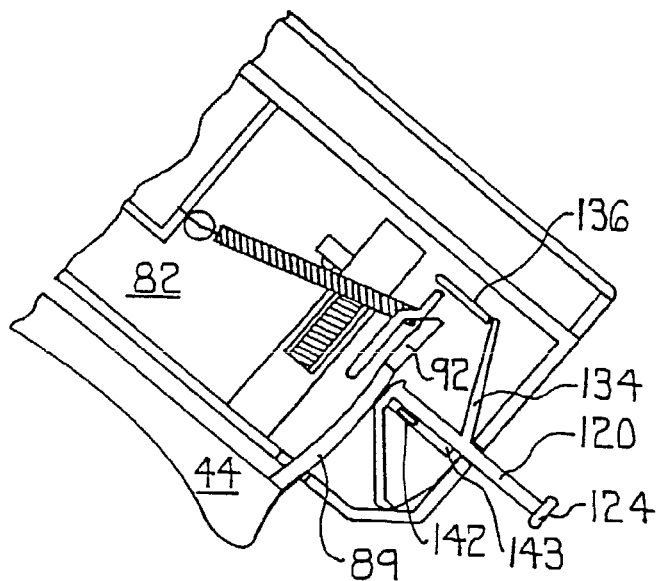
FIGS. 7A and 7B illustrate how the trigger lock cooperates with the other components internal to the handpiece that lock the irrigator into its high speed operating state.

Handpiece 22 further includes a trigger lock 118, now described by reference to FIGS. 5, 7 and 7A, that holds trigger 44 in the fully depressed/high speed operating position. Trigger lock 118 has a flat, rectangularly shaped base 120 that extends into the handpiece 22 through a slot 122 formed rear end of the handpiece. A foot 124 extends perpendicularly across the rear end of base 120 to provide a surface against which an individual can place his/her finger. Extending forward from base 120, trigger lock 118 has a neck 126. Neck 126, while coplanar with base 120, is partially offset to one side of the base. The neck 126 is seated in an opening 128 defined in a flange 130 that extends into the center of the handpiece from right shell 82. Opening 128 is closed by a smaller flange 132 integral with left shell 84 that is aligned with flange 130.

Trigger lock 118 is further formed with a flexible, cantilever spring arm 134 that extends upwards and forwards from the interface between base 120 and neck 126. In order to facilitate the flexible nature of spring arm 134, trigger lock 118 is formed so that spring arm is relatively thin in comparison to the thickness of base 120 and neck 126. For example, in one version of the invention, trigger lock 118 is formed from high impact polystyrene plastic, base 120 and neck 126 have a thickness of approximately 0.080 inches and spring arm 134 has a thickness of approximately 0.014 inches. The upper edge of spring arm 134 abuts a horizontally extending flange 136 that extends into the center of the handpiece from right shell 82. Owing to the flexible nature of spring arm 134, when trigger lock 118 is pressed forward, the action of the spring arm 134 abutting flange 136 places a rearward-acting force on the trigger lock.

The trigger lock 118 further includes a head 138 that is located adjacent the forward end of neck 126. Head 138 extends perpendicularly across neck 126 to project above the upper surface of the neck. There is also a web 140 that extends downwardly from neck 126. Web 140 is formed to define a slot 143 immediately below neck 126. When trigger lock 118 is fitted in handpiece, a lower, horizontally aligned portion 142 of flange 130 extends through slot 143. This horizontal portion 142 of flange 130 thus provides structural support to hold trigger lock 118 in place. Web 140 itself provides structural rigidity to the neck 126. In the illustrated version of the invention, a flange 144 extends perpendicularly across the forward edge of web 140. Flange 140 is integral with head 138.

Figure 7B:
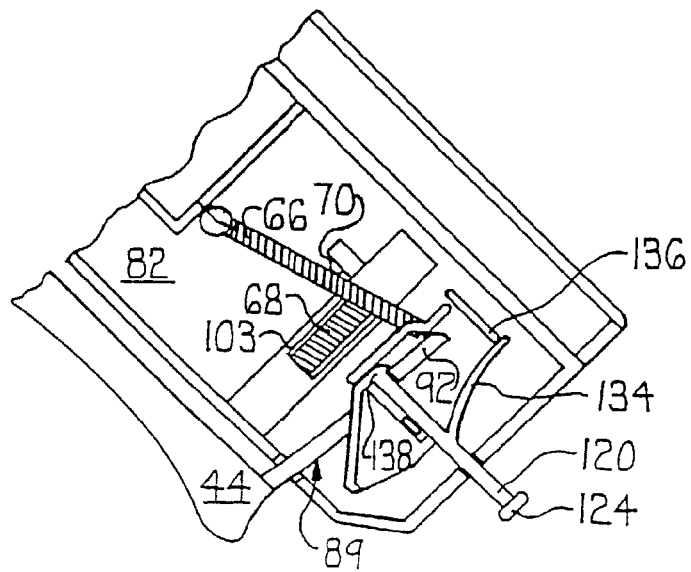

After trigger 44 is placed in the high speed operating position, trigger lock 118 is employed to lock it in this position as depicted by FIG. 7B. The person wanting to so set the irrigator 20, presses in on the exposed portion of the trigger lock 118 to cause its forward movement. The forward displacement of the trigger lock 118 positions its neck 126 under the foot 92 of the trigger 44. Downward movement of the trigger 44 upon the release of an actuating grasp is stopped by the trigger lock 118. Instead, the trigger 44 is locked in position so as to hold spring 66 against contact 70. Irrigator 20 is unlocked from the high speed operating state by pressing upwardly on the trigger 44. Once the foot 92 of the trigger 44 clears head 138 of the trigger lock 118, spring arm 134 exerts sufficient force on the trigger lock 118 to move the trigger lock rearwardly, away from the trigger 44. The return of the trigger lock 118 to its initial position allows trigger 44 and spring 66 to be returned to their low speed or off operating positions.

As seen in FIGS. 2 and 8, pump 24 has its own sleeve-like, open ended discharge head 150. Pump 24 is seated in the forward end of the handpiece 22 so that discharge head 150 is directed towards the front end of the handpiece and extends out through an opening, (not identified,) defined by shells 82 and 84. A tip lock 152, seen in FIGS. 8 and 9, is positioned in the front of the handpiece 22 immediately forward of pump discharge head 150 for securing the tip assembly 30 to the handpiece. The tip lock 152 is formed from a single piece of flexible plastic such as a high impact polystyrene. Tip lock 152 is shaped to have a flat face plate 153 that is located in front of the open end of the pump discharge head 150. Face plate 153 is provided with an oval opening 154 through which the rear end of the discharge tube 32 is inserted into the discharge head 150. It will be further noted that the portion of face plate 153 that defines opening 154 has a beveled surface 155 around the upper portion of the opening 154. Tip lock 152 further includes an arcuately shaped base plate 156 that extends perpendicularly rearward from face plate 153. In the illustrated version of the invention, base plate 156 is provided with raised members 158 to facilitate manual depression of tip lock 152. A spring plate 160 integrally formed with tip lock 152 extends rearwardly from the top edge of face plate 153. Tip lock 152 is molded so that in its unbiased state, spring plate 160 projects approximately 96° away from face plate 153.

The upper two-thirds of tip lock 152 are seated within opposed L-shaped brackets 162 that extend forward from shells 82 and 84. Brackets 162 form the most forward facial surface of the front end of handpiece 22. The tip lock 152 is held in place by opposed L-shaped three-sided ribs 164 integral with shells 82 and 84. When the handpiece 22 is assembled, ribs 164 block downward movement of the spring plate 160 so as to prevent tip lock 152 from falling out of the handpiece. The base plate 156 is, however, exposed for manual displacement. Shells 82 and 84 are further formed to define a biasing bar 166 that extends across the width of the handpiece 22. Biasing bar 166 is positioned so as to abut the rear end of spring plate 160. Biasing bar 166 is thus the component internal to the handpiece 22 that acts in opposition to spring plate 160 to urge tip lock 152 downwardly.

Figure 3:
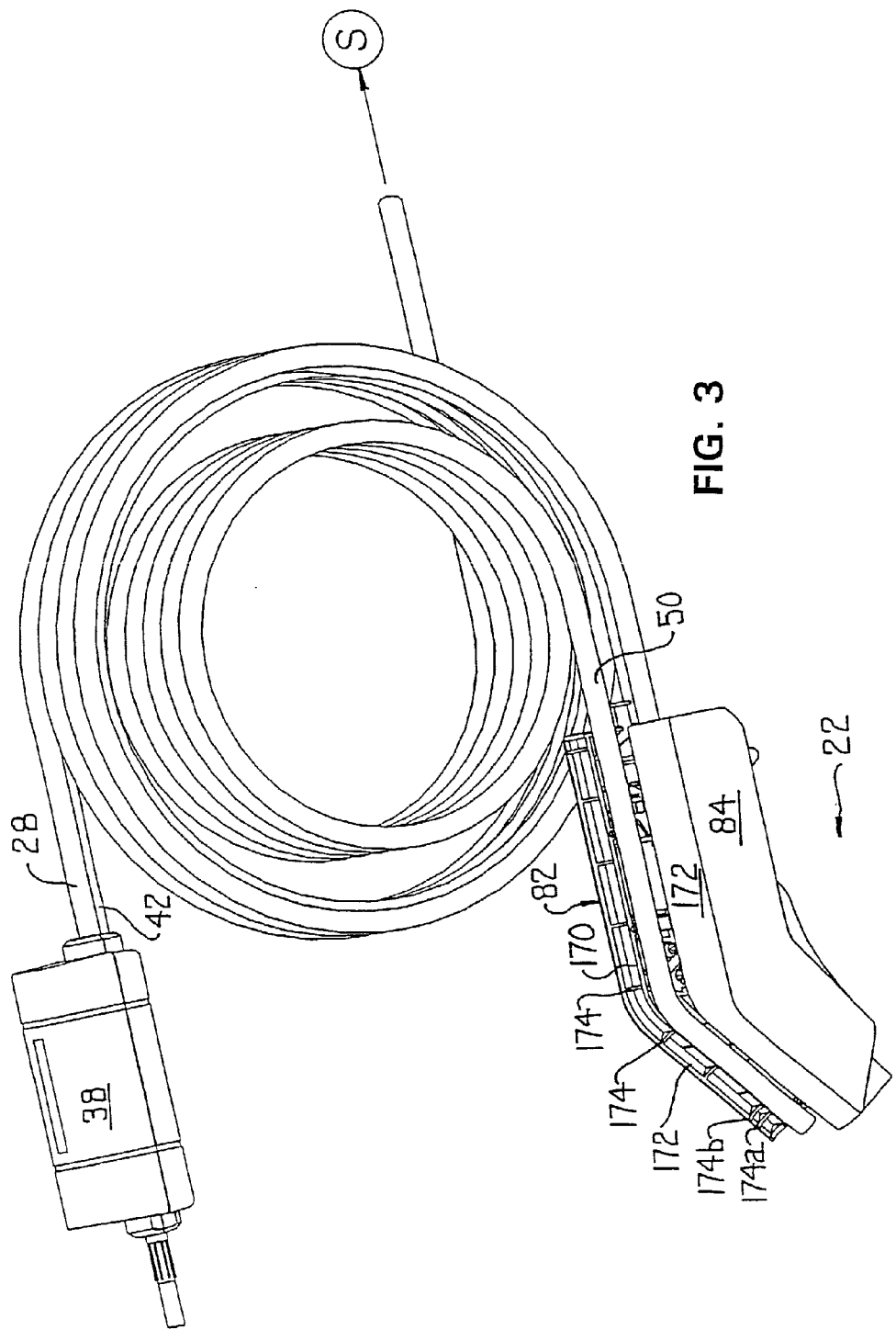
FIG. 3 is a perspective view illustrating the relationship of the drain tube to the handpiece.

Drain tube 50, as seen in FIG. 3, is seated in an elongated channel 170 that extends along the top of handpiece 22. Channel 170 is formed by two external spines 172, each spine being integrally formed with a separate one of shells 82 and 84. Each spine 172 extends the length of the shell 82 or 84 above the portion of the shell 82 or 84 that forms the enclosed body of the handpiece 22. In the depicted version of the invention, spines 172 are formed as curved walls. Also integral with shells 82 and 84 are webs 174, seen in FIGS. 3 and 9, that extend from the inner walls of spines 172 to the adjacent outer surfaces of the shells. Webs 174 are formed to have curved outer surfaces that define the circular cross-sectional profile of channel 170. Spines 172 are formed so that the there are pairs of opposed webs 174 integral with the shells 82 and 84 that are in planar alignment. Spines 172 are further dimensioned so that the top surfaces thereof do not abut.

When handpiece 22 is assembled, drain tube 50 is seated between shells 82 and 84 so as to be seated in channel 170. The opposed webs 174 impose a slight inwardly directed force of the drain tube 50 so as to compress and secure the drain tube 50 to the handpiece. When the tip assembly 30 is coupled to the handpiece 22, suction tube 48 seats in the front end of the drain tube 50. In preferred versions of the invention, shells 82 and 84 are formed so that the two most forward webs, webs 174a and 174b, are positioned rearwardly away from the portion of the drain tube 50 in which the suction tube 48 is seated. This positioning ensures that, when the tip assembly 30 is coupled to the handpiece 22, the compression force developed by webs 174a and 174b holds drain tube 50 in place.

Figure 10:
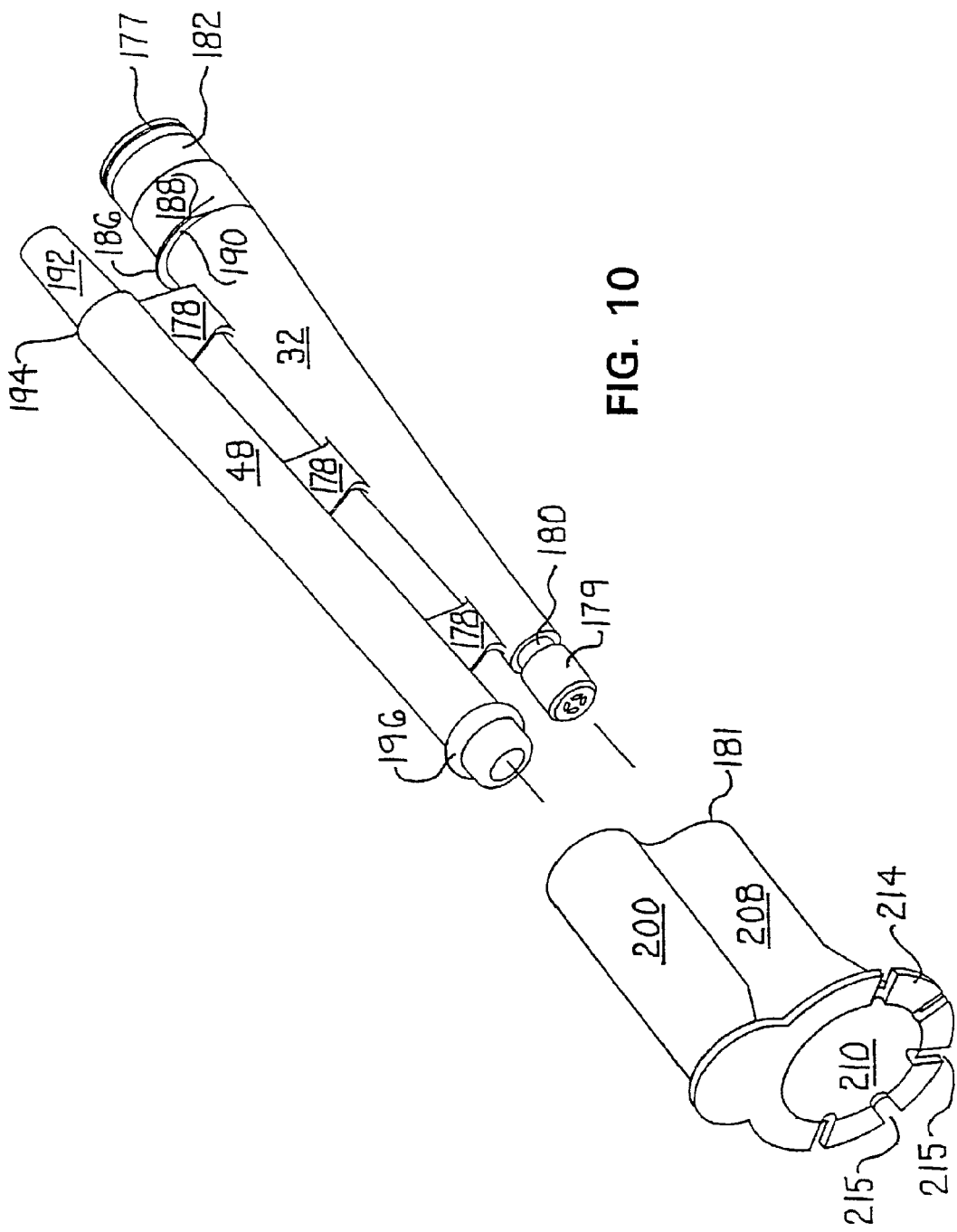
FIG. 10 is a view depicting the basic components of the removable tip assembly including the detachable spray shield.

FIGS. 1 and 10 illustrate the basic components of tip assembly 30. The discharge tube 32 and the suction tube 48 are connected to each other by a set of spaced apart webs 178. A nozzle 179 is fitted over the open forward end of the discharge tube 32 to direct the stream of fluid discharged therefrom. It will be noted that the nozzle 179 is constructed to define an annular groove 180 around the front end of the discharge tube 32. A spray shield 181 is removably fitted over the open ends of the depicted tube assembly. The rear end of the discharge tube 32, the end that is fitted into the handpiece 22, is provided with a neck 182 that has a reduced outer diameter in comparison to the immediately adjacent portion of the tube. An O-ring 177 is fitted in a groove, (not identified,) formed immediately inward of the open end of the neck 182. The rear end of discharge tube 32 is further formed so as to have an upwardly extending flange 186. Flange 186 extends from a portion of the base having the relatively large outer diameter, as opposed to the reduced diameter neck 182, and extends upwards towards suction tube 48. The flange 186 is shaped so as to have a first tapered surface 188 that extends from the portion of the tube adjacent neck 182. The opposed surface of the flange extends at a right angle away from the discharge tube so as to form a 90° step 190.

The rear end of the suction tube 48 is formed to have a neck 192 with a reduced outer diameter. More particularly, it can be seen that the neck 192 is narrowest at its open end, the end seated in drain tube 50, and widest around the portion that is closest to the rest of suction tube 48. In the depicted version of the invention, a pronounced circular step 194 separates neck 192 from the rest of the suction tube 48 though that may not always be the case. It should be understood that while the outer diameter of neck 192 is less than the outer diameter of the main portion of discharge tube 48, the inside wall of the tube, including neck 192, is of constant diameter. An annular rib 196 extends around the outer surface of suction tube 48 immediately rearward of the front end of the tube. The purpose of rib 196 will be explained hereinafter.

Figure 10A:
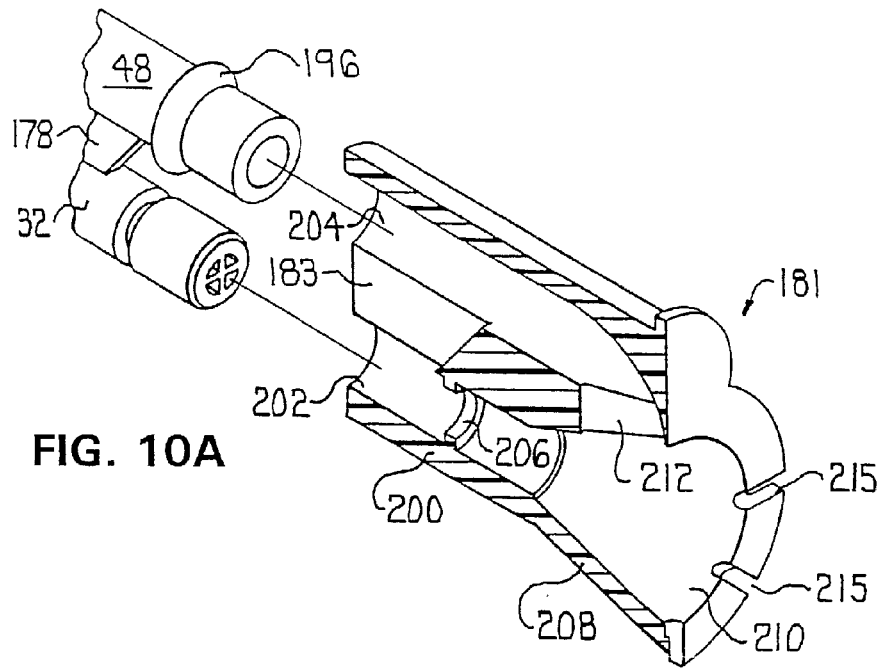
FIG. 10A is an enlarged view of the front end of the tip assembly depicting the removable shield in a cross-sectional view.

Spray shield 181, now described by reference to FIGS. 10 and 10A, is formed of flexible material such as polyvinyl chloride. The spray shield 181 is formed so as to have a base section 200 of generally oval shape. Base section 200 is formed to define two bores 202 and 204. Bore 202 serves as the discharge bore and is the bore in which the front end of the discharge tube 32 is seated. To facilitate the securement of the spray shield to the discharge tube/suction tube sub-assembly, base section 200 is formed to have an annular lip 206 that extends inside bore 202. When the spray shield 181 is fitted over discharge tube 32, lip 206 engages in the annular groove 180 between the discharge tube 32 and nozzle 179.

Bore 204 serves as the suction bore and is the bore in which the front end of suction tube 48 is seated. Bore 204 is dimensioned so that when the spray shield 181 is seated over the discharge tube 48, annular rib 196 abuts the inner wall of base section 200 that defines bore 204 to form a seal around the end of the bore 204.

The base section 200 is further formed to define a slit 183 that extends between bores 202 and 204 and opens towards the rear of the spray shield 181. When the spray shield is seated on the discharge tube-suction tube sub-assembly, the most forward web 178 seats in slit 183. In some versions of the invention, the web 178 may fully seat in slit 183.

Extending forward from base section 200, spray shield 181 is shaped to have an open-ended discharge head 208. Discharge head 208 defines a generally conically shaped discharge chamber 210. Discharge bore 202 opens into the center of discharge chamber 210, at the apex of the chamber. Suction bore 204 extends forward of the open end of discharge bore 202, curves towards the longitudinal axis of bore 202 and chamber 210 and opens into the side of discharge chamber 210. In preferred versions of the invention, suction bore 204 is in fluid communication with the chamber 210 through an opening 212 located immediately rearward of the edge of the wall defining the open end of chamber 210. Thus, opening 212 is located closer to the open end chamber 210 than the end into which discharge bore 202 opens.

Spray shield 181 is further shaped to have an outwardly directed lip 214 around the open end of discharge chamber 210. Lip 214 is shaped so that a forward surface thereof, the surface that is pressured against tissue, has small channels 215. Channels 215 extend from the outer perimeter of lip 214 to the discharge chamber 210. As seen by the partial depiction of one channel 215 in FIG. 10A, one channel 215 is located diametrically opposite opening 212 across discharge chamber 210.

FIGS. 8 and 11 illustrate how the tip assembly 30 is locked to the handpiece 22. As can be seen in these Figures, tip assembly 30 is positioned towards the front end of the handpiece 22 so that the neck 182 of the discharge tube 32 is inserted through opening 154 of the tip lock 152 and into the discharge head 150 of pump 24. The tip assembly 30 is pushed towards the handpiece 22 until flange 186 of the discharge tube 32 passes through opening 154. As the discharge tube passes through opening 154, tapered surface 188 of flange 186 abuts the complementary beveled surface 155 around opening 154. Further insertion of the discharge tube 32 thus serves to displace the tip lock 152 upwardly. Once flange 186 passes beyond tip lock 152, spring plate 160 forces the tip lock to return to its initial position. Thus, as depicted in FIG. 11, the inner surface of face plate 153 of tip lock 152 seats against step 190 of flange 186 to prevent unintended removal of the tip assembly 30. When the tip assembly 30 is so positioned, O-ring 177 forms a seal between discharge tube 32 and the surrounding inside wall of discharge head 150 of pump 24.

The coupling of the tip assembly 30 to handpiece 22 also results in the coupling of suction tube 48 into drain tube 50. More particularly, as the discharge tube 32 is being locked in position, neck 192 of the suction tube 48 is simultaneously seating in the open front end of drain tube 50. Owing to the outwardly directed taper of neck 192, the neck forms its own compression seal against the inside wall of drain tube 50.

It should be understood that, in some preferred versions of the irrigator 20 of this invention, handpiece 22 and tip assembly 30 are designed so that the distance between the front surface of the handpiece and the trailing edge of the closest web 178 is between 0.015 and 0.075 inches. In still more preferred versions of the invention, this distance is approximately 0.030.

Tip assembly 30 is uncoupled from the handpiece 22 by the simple upward depression of base plate 156 of tip lock 152. This action causes the tip lock 152 to move upwardly relative to the handpiece as illustrated in FIG. 12. This displacement of the tip lock 152 serves to space the portion of face plate 153 that defines the upper portion of opening 154 away from tip assembly flange 186. Once this separation occurs, the tip assembly 30 is simply pulled away from the handpiece 22.

Once the tip assembly 32 is coupled to handpiece 22, the irrigator 20 is ready for use. The person using the irrigator only needs one hand to both grasp irrigator 20 and to depress trigger 44 that controls the on/off state of the irrigator and the rate at which it discharges fluid. Should continual high-speed operation of the irrigator be required, all one needs to do is depress trigger lock 118 to hold the trigger in the correct position. Irrigator 20 is then unlocked from high-speed operation by simple depression of trigger 44.

When suction system 46 is actuated, the suction it draws causes a suction head to develop at opening 212 in the spray shield 181. Since opening 212 is located relatively close to the open end of discharge chamber 210, water and debris are immediately drawn into suction bore 204 upon their movement away from the surface against which the spray shield 181 is placed. This minimizes the extent to which material swirls or otherwise moves through the discharge chamber 210. An advantage of the immediate removal of this material is that it eliminates the extent to which matter in the discharge chamber 210 obstructs the application of pulses of fluid to the surface to which the irrigator 20 is applied.

In versions of the invention wherein the spray shield 181 is provided with channels 215, the channels serve as conduits through which air is drawn into the discharge chamber 210. The venting of air into the discharge chamber around the perimeter of the spray shield-body site interface prevents the tissue still part of the patient from being unintentionally separated from the site to which the irrigator 20 is applied.

Still another advantage of the irrigator 20 of this invention is that spray shield 181 is snap fitted to the rest of the tip assembly 30. This makes it possible to provide different shields that can be used with a single discharge tube-suction tube subassembly. Consequently, a medical facility does not have to maintain an inventory of different tip assemblies, the only difference between the individual assemblies being their spray shields.

The fluid and other material drawn through the suction tube 48 flows into the suction system 46 through drain tube 50. Since neck 192 of suction tube 48 seats in drain tube 50, there is essentially no leakage of the fluid and material as it flows into the drain tube. This is even the case when, owing to side loading, the axis of suction tube 48 angles out of alignment with the axis of the handpiece 22. Moreover, the diameter of the bore through drain tube 50 is greater than the diameter of the bore through suction tube 48. For example, in some versions of the invention, the diameter of the inside wall of suction tube 48 is approximately 0.200 inches and the diameter of the inside wall of the drain tube 50 is 0.250 inches. Thus, the interface between the two tubes 48 and 50 is not a constriction that could potentially serve as a clog point for material passing through the tubes. Moreover, owing to the positioning of drain tube 50 along the upper outer surface of the handpiece 22, the degree of curvature of the tube is kept to a minimum. In many preferred versions of the invention, the handpiece is formed so that drain tube 50 subtends an arc of greater than 90° and, more preferably, approximately 140° and the inner radius of the tube is greater than 0.75 inches and, in still more preferred versions of the invention, between 0.85 and 0.90 inches. Also, since there is not a "third" tube, connecting the portion of the drain tube 50 internal to the handpiece 22 with its downstream extension, the need to provide an additional fluid connection port to the handpiece is eliminated. The elimination of this fluid connection port, in addition to its cost savings, eliminates another connection point at which the material in the drain tube 50 could potentially clog the tube. Thus, the irrigator 20 of this invention is further designed to minimize the extent to which the material drawn through drain tube 50 will clog the tube.

Still another feature of this invention is that since spines 172 do not abut, drain tube 50 is visible along the top of the handpiece 22. The drain tube 50 itself is formed out of transparent material. Thus the person using the irrigator need only look down at the handpiece to view the material being drawn away from the site at which the irrigator is applied. This visual exposure of the drain tube 50 further makes it possible for medical personnel to monitor fluid and material flow through the portion of the drain tube disposed in the handpiece 22.

Figure 13:
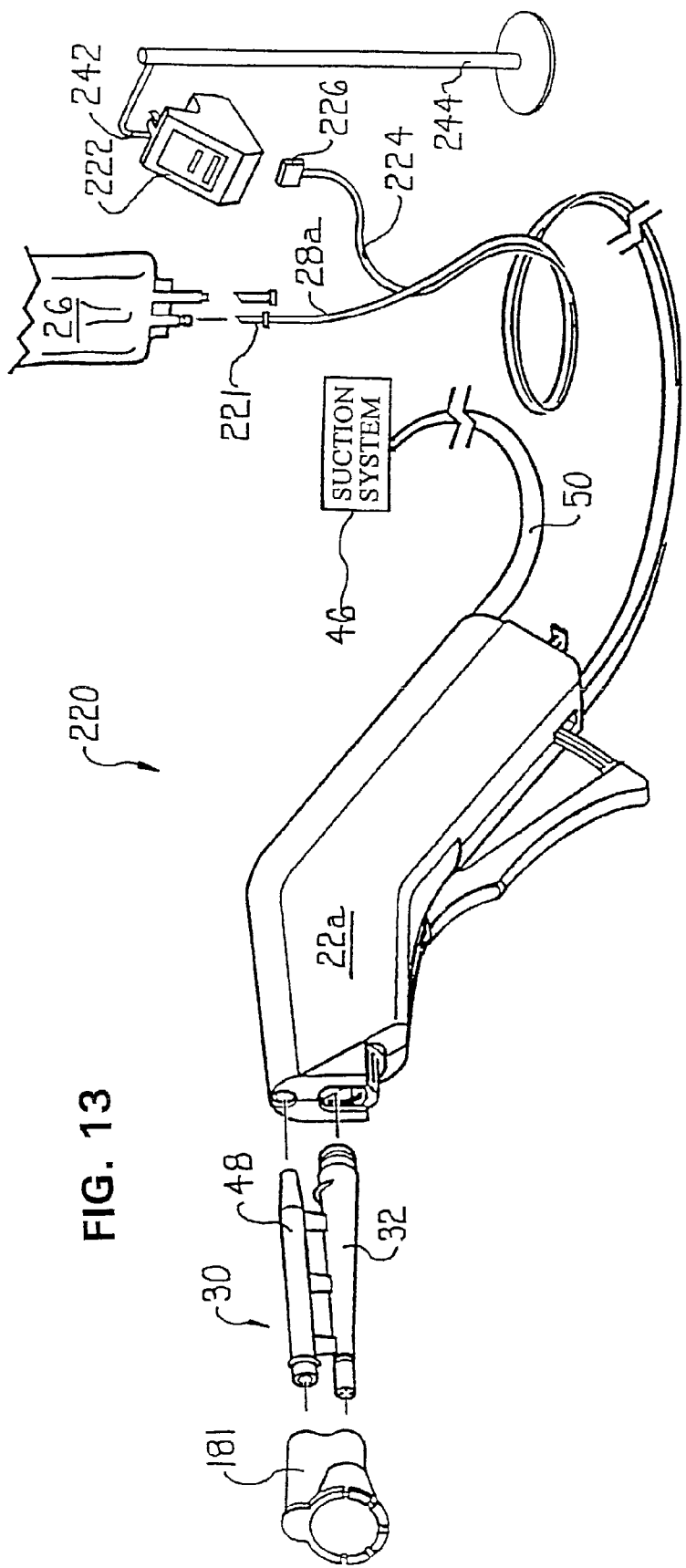
FIG. 13 is a view of an alternative irrigator of this invention wherein the handpiece is powered by a rechargeable battery pack.

An alternative irrigator 220 of this invention is now initially described with respect to FIG. 13. Irrigator 220 includes a handpiece 22a that is physically similar in structure and function to above described handpiece 22. Tip assembly 30 is attached to the front of handpiece 22a to provide the tubes that serve as conduits through which fluid is discharged from the handpiece and a suction head is presented at the site to which the irrigator is applied. Irrigating fluid is supplied to handpiece 22a from bag 26 through supply tube 28a. A spike 221 located at the end of the supply tube 28a makes the fluid connection between the bag 26 and the tube. Power for energizing the handpiece 22a comes from a power pack 222 that is positioned outside the sterile field in which the handpiece 22a and tip assembly 30 are employed. The current from power pack 222 is applied to the handpiece 22a through a power cable 224. Power conductors 60a and 62a and ground conductor 64a (FIG. 16) are disposed within power cable 224. A plug 226 at the end of power cable 224 plugs into a complementary socket 228 in the power pack 222. In many preferred versions of the invention, the portions of the supply tube 28a and power cable 224 that extend from handpiece 22a are adhesively secured together. Often power cable 224 is longer than supply tube 28a to allow the power pack 222 to be placed at a more distal location to the sterile field at which the irrigator 220 is being used than bag 26. The adhesive employed to secure the supply tube 28a and power cable 224 is selected to allow these conduits to be readily separated to the extent needed to facilitate the placement of the power pack 222 outside of the sterile field.

Figure 14:
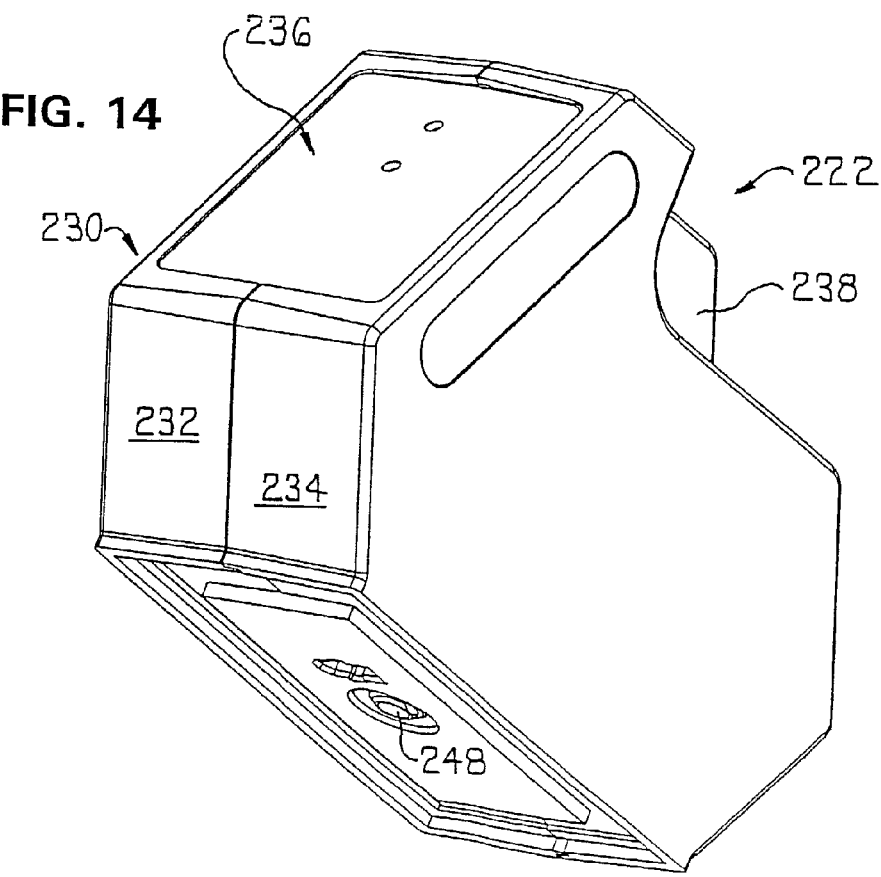
FIG. 14 is an isometric, upwardly oriented view of the rechargeable battery pack.
Figure 15:
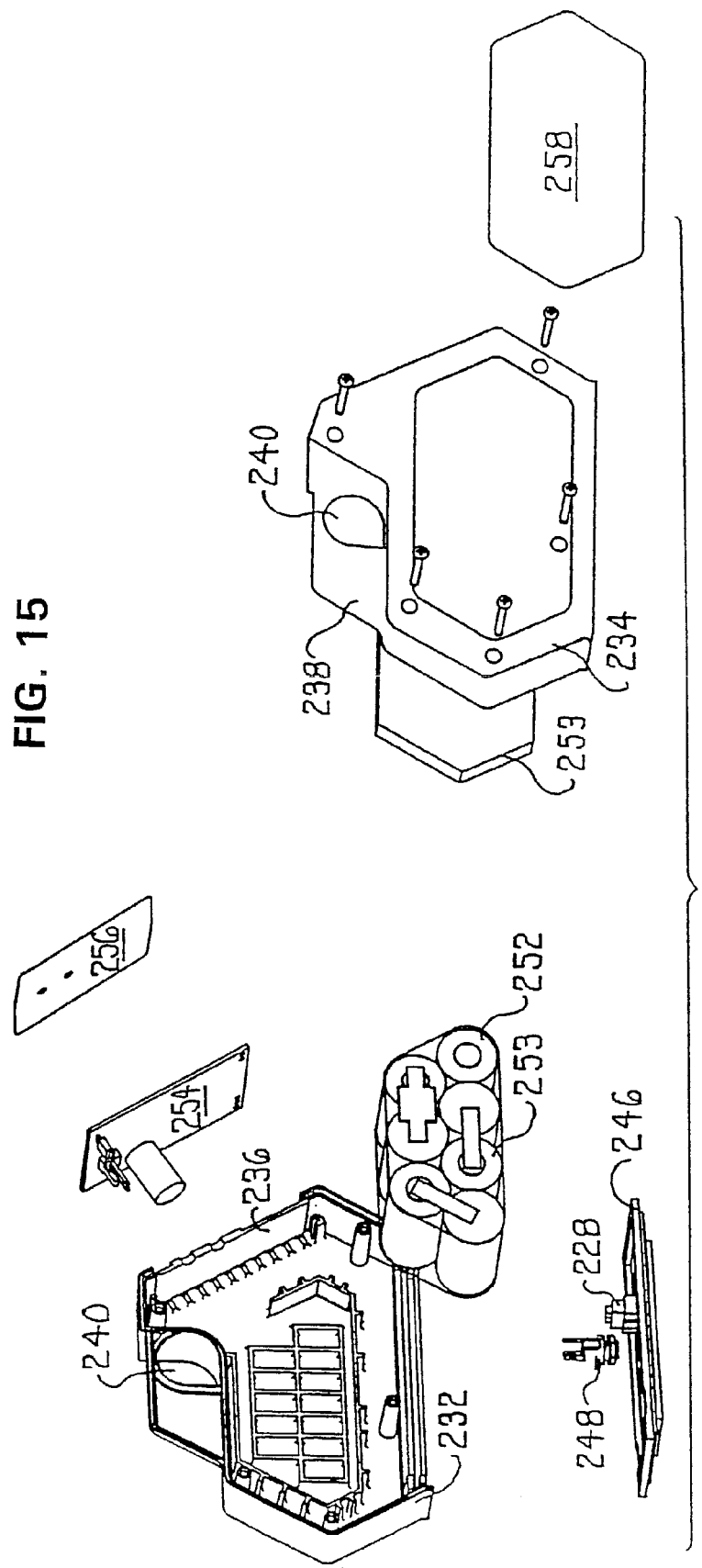
FIG. 15 is an exploded view of the components internal to the rechargeable battery pack.

The power pack 222, as seen in FIGS. 14 and 15, includes a housing 230 formed out of two shells 232 and 234 and a base plate 246. Shells 232 and 234 are formed to provide the housing 230 with an indicator face 236 that extends diagonally away from the bottom surface of the power pack 222. A handle 238 with a finger hole 240 extends downwardly below the portion of the housing 230 that defines indicator face 236. Finger hole 240 performs two functions. First, it provides an opening for a person to grasp the power pack 222 so that it can be easily handled. Secondly, finger hole 240 serves as a opening which allows the power pack 222 to be mounted to a horizontally extending arm 242 of an IV pole 244 in a surgical suite (FIG. 13).

A base plate 246 is secured between shells 232 and 234 and forms the bottom surface of the power pack 222. A DC power plug 248 is mounted to base plate 246 to provide a connection between a charger, (not illustrated) and the power pack 222. When the power pack 222 is charged, base plate 246 is positioned against a complementary surface of the charger from which a charger plug, complementary to plug 248, extends.

Power pack 222 is further shaped so that socket 228 to which power cable plug 226 is connected is also fitted to base plate 246. This arrangement ensures that, when the power pack 222 is plugged into the charger, it cannot simultaneously be used to energize the handpiece 22a. This prevents current from being directly supplied from the charger, which may not have the voltage protectors required for real-time patient connection, to the handpiece 22a.

Internal to the power pack 222 is a cluster of rechargeable cells 252. In the depicted version of the invention, power pack 222 is provided with seven series connected NiCad cells 252. Each cell 252, when fully charged can develop a potential of 1.2 Volts. A foam pad separates cells 252 from shell 234. A circuit board 254 is mounted below the portion of the housing 230 that defines indicator face 236. Circuit board 254 carries the components forming the circuitry that regulates the charging and discharging of cells 252. FIG. 15 further illustrates the label 256 positioned over indicator face 236 and the label 258 positioned over the side of the housing 230.

In preferred versions of the invention, power pack 222 is designed to have a center of gravity that is below and aligned with the center of finger hole 240. This construction facilitates the balancing of the power pack 222 when it is suspended from arm 242 of the IV pole 244.

FIG. 16 is a block diagram of the circuitry internal to power pack 222 that controls the charging and discharging of cells 252. The DC power plug 248, represented as opposed terminals, is connected to a cell charger 264. The cell charger 264 charges the cells 252 at one of two rates as a function of the potential across the cells.

Power pack 222 is configured to provide a pulse width modulated DC signal to handpiece 22a. The pulse is nominally one of two widths and is a function of the setting of the spring 66 internal to handpiece 22a. More particularly, when spring 66 is connected to conductor 60a, pulses having a relatively long "on" period are applied to the handpiece 22a; these pulses function as a high speed drive signal to the handpiece. When spring 66 is connected to conductor 62a, pulses having a relatively short "on" period are applied to handpiece 22a; these pulses function as a low speed drive signal to the handpiece. The potential of the low speed drive signal applied to motor 34 is further reduced to the extent spring 66 is in series with resistor 68.

The potential across the cells 252 is applied to handpiece 22a through either power conductor 60a or 62a and ground conductor 64a, all internal to power cable 224. The positive terminal of the cluster of cells 252 is connected to either power conductor 60a or power conductor 62a through a slow speed driver 266. Ground conductor 64a is selectively tied to the ground internal to the power pack 222 through a FET 268. The on/off period of FET 268 controls the width of the DC pulses applied to the handpiece 22a.

The on/off state of FET 268 is set by a speed regulator 270. The output signal produced by speed regulator 270 is itself a function of signals received from an oscillator 272; and a slow speed detector 274. Speed regulator 270 further monitors the potential across the cells 252 to adjust pulse width as a function of cell potential.

Oscillator 272 produces a constant frequency output signal. The output signal produced by oscillator 272 is, however, forced to ground if a power down circuit 276 determines that the voltage across the cluster of cells 252 has fallen below a set potential. The slow speed detect circuit 274 produces a slow speed signal based on the detection of one of either two signals states. First, slow speed detector 274 produces a slow speed signal when the slow speed driver 266 produces a signal indicating current is being supplied to the handpiece 22a through low speed power conductor 62a. Secondly, slow speed detector 274 produces the slow speed signal when it determines that the potential across the cluster of cells 252 has fallen below a set potential.

Figure 17A:
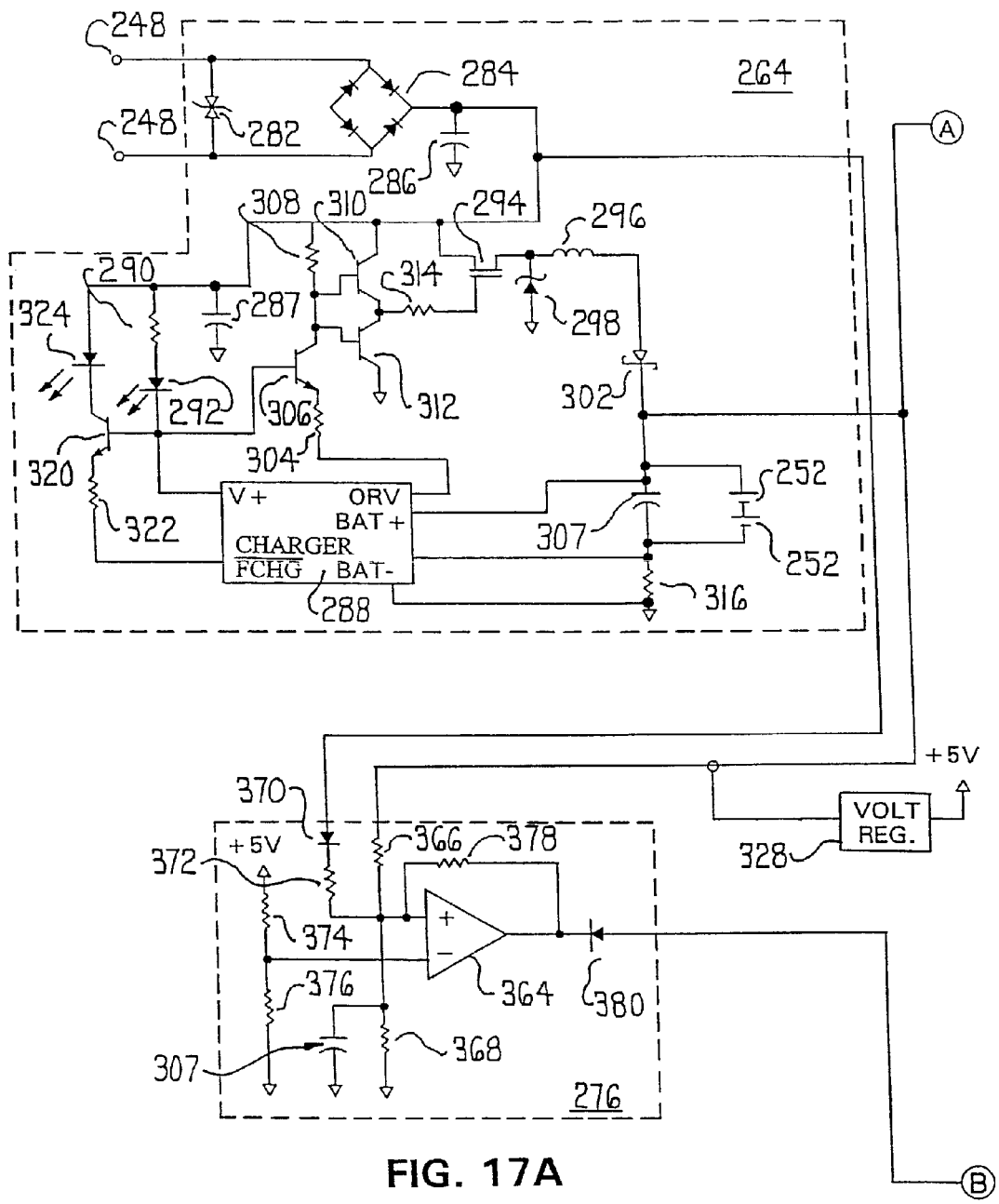
FIGS. 17A and 17B are assembled together to form a schematic diagram of the electronic circuitry of FIG. 16.
Figure 17B:
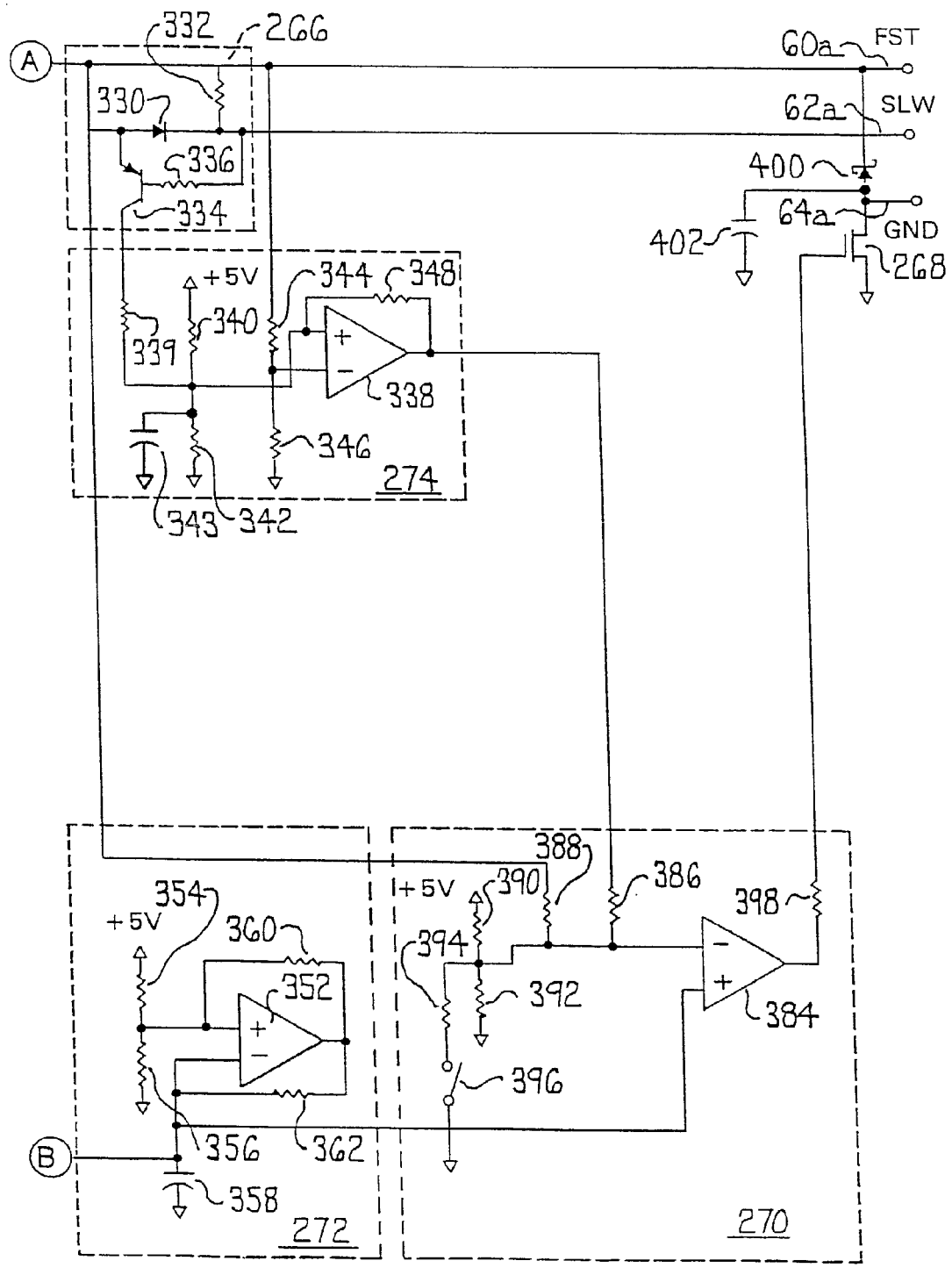

FIGS. 17A and 17B, when assembled together, form a schematic drawing of the electrical components internal to the power pack 222. Cell charger 264 includes a voltage suppressor 282 that is tied across the opposed terminal of the DC power plug 248. Whenever the potential across the DC power plug 248 exceeds a preset voltage, voltage suppressor 282 establishes a closed circuit across the power plug 248 to prevent excessive voltages from being applied to the other components internal to the power pack 222. A full-wave bridge rectifier 284 is also tied across the terminals of the DC power plug 248. Rectifier 284 performs two functions. First, it allows an AC signal to be applied to the power pack 222 for recharging the cells 252. Secondly, in the event the polarities of the DC signal applied to power plug 248 are reversed, it ensures that the positive signal is still applied to the other components of the cell charger 248. A filter capacitor 286 is tied between the output terminal of rectifier 284 and ground to minimize voltage variations in the signal, the rail voltage, distributed downline from the rectifier. In the illustrated version of the invention, the rail voltage is further filtered by a capacitor 287 also tied between the rectifier 284 and ground. In preferred versions of the invention, an 18 to 35 VDC signal or a 15 to 25 VAC signal is applied to cell charger 264 in order to charge cells 252.

The rail voltage from rectifier 284 is applied to the V+ terminal of a charging chip 288 designed regulate the charging of cells 252. One particular charging chip 288 that can be employed as part of this invention is the MAX713 manufactured by Maxim. The signal from rectifier 284 is applied to charging chip 288 through a resistor 290 and a forward biased LED 292. The emission of light by LED 292 serves as an indication that a charging current is being applied to the power pack 222. Not shown are the program pin connections and voltage divider associated with charging chip 288 that are used to set the various signal transitions of the charging chip described hereinafter.

The actual current employed to charge cells 252 comes from rectifier 284 through a buck converter consisting of FET 294, inductor 296 and diode 298. The FET 294 and inductor 296 are series connected together and are connected to the cells 252 through a forward biased diode 302. Diode 298 is a reverse biased catch diode that is connected between the junction of FET 294 and inductor 296 and ground. The signal that turns FET 294 on and off is based on a DRIVE (DRV) signal generated by charging chip 288. The DRIVE signal is applied to a resistor 304 and from the resistor to the emitter of transistor 306. The collector of transistor 306 receives the rail voltage from rectifier 284 through a resistor 308. The base of transistor 306 is tied to the cathode of diode 292 to receive the V+ signal. Collectively, resistors 304 and 308 and transistor 306 level shift the rail voltage to a set voltage below rail voltage. In some versions of the invention, this difference is approximately 10 VDC. The actual times at when the level-shifted voltage is present at the collector of transistor 306, is a function of the assertion of the DRIVE signal.

The signal present at the collector of transistor 306 is applied to the bases of two series-connected transistors 310 and 312 that act as current drivers. The collector of transistor 310 is tied to rectifier 284 to receive the rail voltage. The emitter of transistor 310 is tied to the emitter of transistor 312. The collector of transistor 312 is tied to ground. The current-boosted signal present at the junction of emitter-emitter junction of transistors 310 and 312 is applied to the gate of FET 294 through a resistor 314.

Charging chip 288 asserts the DRIVE signal to cause the cells 252 to be charged at either a slow, "trickle," rate or a fast rate. The rate at which the charging chip 288 allows the cells to be charged is a function of the potential across the cells, current flow through the cells and the period of time cell charger 264 operates in at the fast rate. Charging chip 288 has BAT+ and BAT− terminals that are connected directly across the cells 252 through which the chip monitors the potential across the cells. A capacitor 307 is also tied across the cells 252. The negative terminal of the cells 252 is connected to ground through a resistor 316. Charging chip 288 has a ground terminal that is connected to ground at the point resistor 316 is connected to ground. Charging chip 288 thus measures current flow through cells 252 as a function of the voltage between its BAT− and ground terminals. The charging chip basis its charging of the cells 252 in part on this current flow measurement.

The charging chip 288 also asserts a FAST-CHARGE (FCHG) signal whenever it is charging the cells 252 at the trickle rate. The FAST-CHARGE signal is applied to the emitter of a transistor 320 through a resistor 322. The collector of transistor 320 receives the rail voltage from rectifier 284 through a forward biased LED 324. The base of transistor 320 is tied to the cathode of LED 292.

When cells 252 integral with power pack 222 are initially charged, cell charging chip 288 trickle charges the cells. This is accomplished by cycling the DRIVE signal so that it is on a relatively small fraction of time. When the DRIVE signal is on, FET 294 is turned on to allow inductor 296 to charge. During this part of the charging cycle current flows to the cells 252 so as to charge the cells. During trickle rate charging, the DRIVE signal is cycled at a rate so that when FET 294 is turned off, inductor 296 fully discharges through diode 298. Consequently, during subsequent cycles when FET 294 is on, less current flows through inductor 296 to the cells 252. In one version of the invention, the current supplied to the cells during trickle rate charging is 0.062 Amps.

During trickle rate charging, the FAST-CHARGE signal is asserted high by charging chip 288. Consequently there is no current flow through transistor 320 and LED 324. The LED 324 thus does not emit light.

Charging chip 288 monitors the potential across the cells 252 to determine if it reaches a level at which the cells can accept a higher current charge without being damaged. In one particular version of the invention, for the cells 252 to be fast charged, they must each have a potential of 0.4 Volts. Once charging chip 288 determines this potential, 2.8 Volts for the seven cells, has been reached, the on cycle time for asserting the DRIVE signal is increased; the cell charger 264 enters the fast charge mode.

The increase in the on cycle time for the DRIVE signal causes a like increase in the total percent of time in each cycle FET 294 is turned on. Specifically, charging chip 288 asserts the DRIVE signal for sufficient periods of time so that FET 294 is turned on for sufficient periods of time to ensure that inductor 296 does not fully discharge. Thus, during the periods of time FET 294 is turned on, there is substantially higher current flow to the cells 252 than when the cell charger 264 is operated in the trickle mode. In one particular version of the invention, when cell charger 264 is operated in the fast charge mode, current flow to the cells 252 is approximately 0.5 Amps.

When the cell charger 264 is in the fast charge mode, charging chip 288 negates the FAST-CHARGE signal low. The negation of the FAST-CHARGE signal turns on transistor 320 which, in turn, causes current to flow through LED 324. The current flow through LED 324 serves to cause the LED to emit a light indicating that the power pack 222 is being fast charged.

Cell charger 264 stays in the fast charge mode until one of three events occur. One event is the sensing by the charging chip 288 of a drop in the voltage across cells 252. This voltage drop is interpreted by the charging chip 288 that the cells 252 are fully charged as an evidenced by the drop in current out of the cells. Secondly, charging chip 264 monitors the cells 252 for the voltage across the cells. In some versions of the invention, if this voltage reaches 14 Volts, the cell charger 264 ceases fast mode charging of the cells 252. Thirdly, charging chip 288 monitors the time the cell charger 264 is in the fast charge mode. If the time significantly exceeds the total time expected to fully charge the cells 252, fast mode charging is terminated. In one version of the invention, the time for fully charging the cells is approximately 180 minutes; in these versions of the invention charging chip 288 is programmed to terminate fast mode charging after approximately 264 minutes. Once fast mode charging is terminated, charging chip 288 continues to assert the DRIVE signal necessary to trickle mode charge the cells 252. The continual trickle mode charging of the cells 252 prevents the cells from losing their charge.

The charging/discharging circuit internal to power pack 222 also includes a voltage regulator 328. Voltage regulator 328 is connected to the positive terminal of the cluster of cells 252. The voltage regulator produces a constant level +5 VDC signal that is used as a reference voltage and an operating voltage by the other components internal to the power pack 222.

The slow speed driver 266 is connected to the positive terminal of the cluster of cells 252. Conductor 60a, the conductor over which the high speed drive signal is supplied to the handpiece 22a, is connected directly to the cells 252 through the slow speed driver 266. Conductor 62a, the conductor over which the low speed drive signal is supplied to the handpiece 22a, is connected to cells 252 through a forward biased diode 330. A resistor 332 is connected across the extension of conductor 60a internal to slow speed driver 266 and the cathode of diode 330.

Slow speed driver 266 also includes a transistor 334. The emitter of transistor 334 is tied to the anode of diode 330. The base of transistor 334 is tied to the cathode of diode 330 through a resistor 336. The collector of transistor 334 is tied to the slow speed detector 274 to provide a signal whenever current flow to the handpiece is through conductor 62a.

The slow speed detector 274 includes a comparator 338 that provides a specific signal to indicate if the low voltage drive signal is to be outputted by power pack 222. The signal present at the collector of transistor 334 is applied to the noninverting input of comparator 338 through a resistor 339. In the illustrated version of the invention, the signal from transistor 334 is offset by the signal present at the junction of two series-connected resistors 340 and 342 which are connected between the +5 VDC source and ground. It will further be noted that a capacitor 343 is tied across resistor 342. Capacitor 343 filters out transient noise in the signal present at the junction of resistors 339, 340 and 342. Other capacitors are likewise tied to certain of the other resistors tied to ground. Since the position and purpose of these capacitors are understandable, they will not be further illustrated or described to minimize the complexity of this description and the accompanying drawings.

The voltage across the cluster of cells 252 is applied to the inverting input of comparator 338. More particularly, the voltage across the cells 252 is applied to comparator 338 through a resistor 344. A resistor 346 is tied between the inverting input of comparator 338 and ground. A feedback resistor 348 is tied between the output of comparator 338 and the noninverting input to provide hysteresis damping of the transitions of the output signal from the comparator.

Oscillator 272 includes a comparator 352. The oscillator 272 also includes a voltage divider consisting of series-connected resistors 354 and 356 that are connected between the +5 VDC source and ground. The voltage present at the junction of resistors 354 and 356 is applied to the noninverting input to the comparator 352. The inverting input of comparator 352 is tied to ground through a capacitor 358. A resistor 360 provides a feedback loop between the output of comparator 352 and its noninverting input. A resistor 362 provides a feedback look between the output of comparator 352 and is inverting input. Oscillator 272, when energized, produces a triangle-wave output signal having a frequency between 1.0 K Hz and 2.0 K Hz and, more particularly, approximately 1.3 K Hz.

Power down circuit 276 employs a comparator 364 to monitor the voltage across cells 252. The cell voltage is applied to the noninverting input of comparator 364 through a resistor 366. A resistor 368 is tied between the noninverting input of the comparator 364 and ground to provide the appropriate level adjustment to the signal applied to the comparator. The signal from rectifier 284 is also applied to the noninverting input of comparator 364 through a forward biased diode 370 and a resistor 372.

A reference voltage is applied to the inverting input of comparator 364. This voltage is the voltage present at the junction of series-connected resistors 374 and 376 which are connected between the +5 VDC source and ground.

A feedback resistor 378 is connected between the output of comparator 364 and its noninverting input. A diode 380 is connected between output of comparator 364 and the junction of oscillator comparator 352 and capacitor 358. Diode 380 is reverse biased relative to comparator 364.

Speed regulator 270 provides the signal that turns FET 268 on and off. The on/off signal to FET 268 is produced by a comparator 384. The input to the noninverting input of comparator 384 is the signal present at the junction of comparator 352, capacitor 358 and diode 380. One input to the inverting input of comparator 384 is the output signal from comparator 338 of the slow speed detector 274. The signal from comparator 338 is applied to comparator 384 through a resistor 386. A second input to comparator 384 is the voltage across the cells 252 which is applied to the comparator 384 through a resistor 388. The signal from resistor 388 is a compensation signal which compensates for the changes in the signal from the slow speed detector 274 as function of voltage changes across the cells 252.

The signal applied to the inverting input of comparator 384 is level adjusted by the signal present at the junction of series connected resistors 390 and 392. Resistors 390 and 392 form a voltage divider between the +5 VDC source and ground. A resistor 394 can be placed in parallel across resistor 392 by the closing of a switch 396 tied between resistor 394 and ground. Resistor 394 and switch 396 allows the signal presented to comparator 384 to be adjusted to allow further control of the on-period of the pulse width modulated signal produced by the power pack 222.

The output signal of comparator 384 is applied to the gate of FET 268 through a resistor 398. A diode 400 is reverse biased between the conductors internal to power pack 222 that are connected to power conductor 60a and ground conductor 64a. A capacitor 402 is connected between the anode of diode 400 and ground.

When handpiece 22a is operated at high speed, current flows from cells 252 directly through the slow speed driver 266 to conductor 60a. Consequently there is no current flow through diode 330. As a result, transistor 334 is turned off and the slow speed driver forwards a zero-voltage signal to the slow speed detector 274. As long as the potential across the cells 252 remains above a select potential, the signal present at the inverting input of the comparator 338 of slow speed detector 274 will be greater than the signal present at the noninverting input. Comparator 338 thus outputs a zero-voltage signal to comparator 384 of the speed regulator 270.

The output signal from oscillator 272 is the signal applied to the noninverting input of comparator 384. During the periods when the oscillator output signal is above the signal present at the inverting input, comparator 384 generates a +5 VDC signal that turns on FET 268. As discussed above, during fast operation of the handpiece 22a, speed regulator 270 presents a zero-voltage signal to the noninverting input of comparator 384. Thus, when the irrigator 220 is in this state, comparator 384 asserts a switch signal to turn FET 268 on for relatively long periods of time. For example, in one version of the invention, FET 268 has an on duty cycle of approximately 85% of each period of the output signal generated by the oscillator 272. This ensures that a relatively high average voltage is presented to the motor 34 as the high speed drive signal.

When the irrigator 220 is operated at slow speed, current flow to the handpiece 22a from cells 252 through diode 330 and conductor 62a. The current flow through diode 330 turns transistor 334 on. The turning on of transistor 334 presents a positive voltage to the noninverting input of comparator 338 of slow speed detector 274. The voltage from transistor 334, when combined with the voltage across resistor 342, is greater than the voltage present at the inverting input of comparator 338. Thus comparator 338 will assert a slow speed signal, a +5 VDC signal, to the inverting input of comparator 384.

The rise in the voltage presented to the inverting input of comparator 384 reduces the percent of time the voltage at that inverting input is greater than the output signal of oscillator 272 presented to the noninverting input. Thus, the percent of time comparator 384 asserts the drive signal to turn on FET 268 is reduced. In some preferred versions of the invention, the on duty cycle of FET 268, falls to approximately 70% of the period of the output signal from the oscillator 272. The increased off time of FET 268 causes power pack 222 to present a relatively low voltage signal, the low speed drive signal, to the handpiece 22a. The potential of the drive signal actually presented to the motor 34 will, of course, be function of the position of spring 66 relative to resistor 68.

It should also be understood that speed regulator 270 also adjusts the on duty cycle of FET 268 as a function of the voltage across cells 252. As the voltage across the cells 252 drops owing to their discharge, the signal presented to the inverting input of comparator 384 through compensation resistor 388 drops. The drop in the level of this signal serves to cause the duty cycle with which the comparator asserts a positive-voltage signal to increase. Thus, as the potential across the cells 252 drops, the on duty cycle of FET 268 increases to ensure that a drive signal with a substantially constant voltage is presented to the handpiece 22a as long as the potential across the cells stays above a given minimum level.

Slow speed detector 274 also asserts the slow speed signal to speed regulator 270 whenever the voltage across the cells 252 drops below a select potential. More particularly, as result of the voltage drop across the cells 252, the signal presented to the inverting input of comparator 338, will drop. If the signal at this inverting input falls sufficiently, it will be below the signal present at the noninverting input. If this drop in relative signal strength occurs, comparator 338 will assert the slow speed signal even though the irrigator is set for fast speed operation. Should this occur, the low speed drive signal will be presented to the handpiece 22a through conductor 60a. In one preferred version of the invention, the components forming the slow speed detector 274 are selected to cause the detector to assert the slow speed command signal when the potential across the cells falls below 7.4 VDC.

The power down circuit 276 inhibits operation of the power pack 222 when the potential across the cells 252 drops to a level below which further discharge might cause damage to the cells. More particularly, as long as the voltage across the cells 252 remains above a select level, the signal present at the noninverting input of comparator 364 will be above the voltage of the signal present at the inverting input. Comparator 364 will thus output a signal that will prevent forward biased current flow through diode 380. In some preferred versions of the invention, comparator will assert an output signal as long as the voltage across the cells 252 remains above approximately 6.0 VDC.

If, however, the voltage across cells 252 falls below the set value, the signal present at the noninverting input of comparator 364 will be less than the signal present at the inverting input. The output of comparator 364 will go to ground. Consequently, current will flow through diode 380 and a ground signal will thus be presented to the noninverting input of comparator 384 of speed regulator 270. Since the signal present at the inverting input of comparator 384 is a positive-voltage signal, the output of comparator 384 will likewise be at ground and hold FET 268 in the off state. The turning off of FET 268 prevents current flow from the power pack 222 to the handpiece 22a.

When the power pack 222 is placed back in its charger, the signal from rectifier 284 is applied to the noninverting input of comparator 364 through diode 370 and resistor 372. The signal from the rectifier 284 will be of sufficient potential to overcome the positive feedback that is supplied to the noninverting input through resistor 378. Thus, the signal from the rectifier 284 causes comparator 364 to again assert a positive-voltage signal.

Irrigator 220 has the same basic advantages as previously described irrigator 22. Irrigator 220 further includes a power pack 222 that can be used to energize the handpiece 22a. In some situations it may be more economical to provide this power pack 222 than a use-once battery pack.

Moreover, owing to the separation of power cable 224 from supply tube 28a, power pack 222 may be held outside of the sterile field in which the other components of the irrigator 220 are used. Thus, the power pack 222 need not be subjected to the sterilization practices used to sterilize medical instruments placed in the sterile field. This further serves to reduce the costs of supplying an energization current to the handpiece 22a of irrigator 220 of this invention.

The power pack 222 itself is especially designed to facilitate its repetitive use. The circuitry internal to the power pack 222 ensures that, even when the handpieces 22a with which it is used are operated at low speed, the cells 252 are evenly discharged. Consequently, the individual cells 252 do not develop separate internal electro-chemical "memories" regarding the magnitude of the charges they store. This ensures that when the power pack 222 is recharged, all the cells 252 will recharge to the greatest extent possible. The full recharging of the cells 252 ensures the power pack 222 will, even after numerous rechargings, be able to deliver the potential required to operate the handpiece 22a at high speed.

Also, the power pack 222 is configured so that when the charge falls, the width of the drive signal increases. Thus, the potential of the drive signal applied to the handpiece remains constant even though the voltage across the cells may be dropping. Since this potential does not vary for, a given trigger setting the discharge of fluid from the handpiece 22a remains constant for a given trigger setting even as the potential across the cells 252 falls. The person using the irrigator 220 of this invention thus is not required to engage in real time adjustment of the trigger setting as a result of the discharge of the cells.

Moreover, once the potential across the cells 252 falls below a first level, slow speed detector 274 causes the power pack to produce low voltage drive signals to the handpiece 22a. This accomplishes two tasks. First, it conserves the charge stored in the power pack 222 to increase the period of time with which it can be used. Secondly, by preventing fast speed operation of the irrigator 220, it provides an indication to medical personnel that the power pack 222 will soon be discharged to the point where it can no longer supply an energization voltage to the handpiece 22a.

The power down circuit 276, as discussed above, prevents operation of the power pack when such operation could potentially cause damage to cells 252. Moreover, often after NiCad cells are discharged, the potential across the cells increases. Power down circuit 276 prevents reactivation of the power pack 222 when the cells 252 are in this state. Thus, power down circuit 276, inhibits the use the power pack 222 even though the real-time potential across the cells 252 provides an impression that they are storing enough charge to energize a handpiece 22a for a significant period of time.

Figure 19:
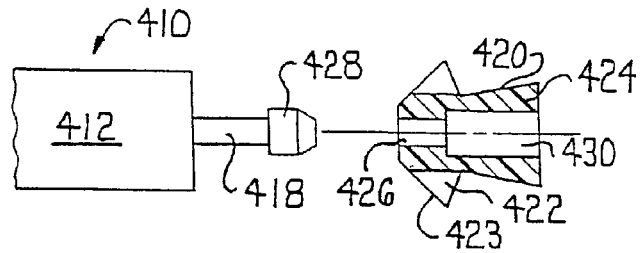
FIG. 19 is a cross sectional view of the rotating head of the nozzle assembly of FIG. 18.
Figure 18:
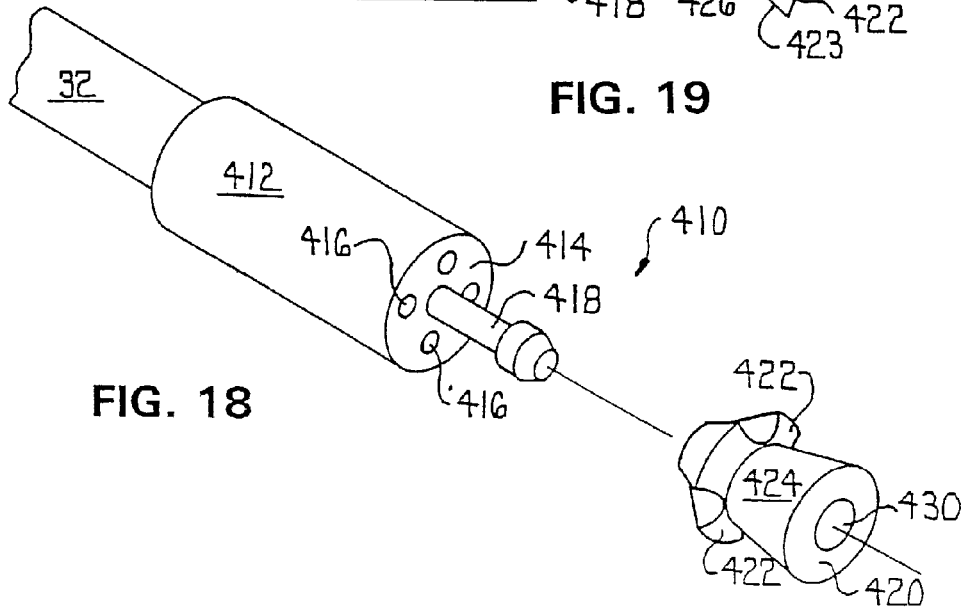
FIG. 18 is a view of a nozzle assembly that may be fitted to the forward end of the discharge tube of a tip assembly of the irrigator of this invention.

FIGS. 18 and 19 illustrate an alternative nozzle assembly 410 that can be fitted to the front end of discharge tube 32 of the tip assembly 30 of this invention. Nozzle assembly 410 includes a cylindrical base 412 that is secured over the open end of discharge tube 32. Base 412 has a front face 414 that is formed with a number of openings 416 through which the irrigating fluid is discharged. A post 418 extends forward from the center of face 414.

A rotating spray head 420 is secured to post 418. The spray head has a body formed out of a number of spaced apart shoulder sections 422. In preferred versions of the invention, the number of shoulder sections 422 equals the number of openings 416 formed in the base 412 of the nozzle assembly 410. The shoulder sections 422 are formed to have bottom surfaces 423 that extend diagonally outwardly from the center of the spray head 420. A nose 424 extends forward from the center of base where the shoulder sections 422 meet. In the illustrated version of the invention, nose 424 is formed with a slight outwardly projecting taper to facilitate the manual grasping and rotation of the spray head 420. The surface of the nose 424, however, does not subtend the spaces between the shoulder sections 422 through which the fluid stream flows.

Spray head 420 is formed with an axially extending bore 426 to facilitate the fitting of the spray head over post 418. The post 418 is formed with its own locking head 428, that is larger in diameter than the post itself, to hold the spray head 420 to the base 412. Nose 424 of the spray head 420 is formed with a counterbore 430 in which the locking head 428 of the post is seated. Typically, the spray head 420 is snap secured over post 418. While not illustrated, in some preferred versions of the invention, locking head 428 and the portion of nose 424 that defines counterbore 430 are formed with interlocking teeth for holding the spray head in a specific position on the post 418.

A tip assembly 30 in which nozzle assembly 410 is installed is used like a standard tip assembly. When the medical personnel want a direct discharge of irrigating fluid onto a body site, spray head 420 is set on post 418 so that the interstitial spaces between the shoulder sections 422 are aligned with openings 416. When spray head 420 is so positioned, the irrigation fluid is discharged through these interstitial spaces so that the fluid is directly discharged onto the body site at which the tip assembly 30 is directed.

When diffused spray is desired, spray head 420 is reset so that shoulder sections 422 are aligned with openings 416. The fluid discharged through the openings thus strikes the base surfaces 423 of the shoulder sections and is diverted radially outwardly toward the surface of the spray shield 181 that define discharge chamber 210 (FIG. 10A.) The fluid is reflected off the spray shield 181 and flows towards the body site.

Tip assembly 30 with nozzle assembly 410 provides either a direct or diffused spray of irrigating fluid. This allows real time adjustment of the spray pattern without requiring medical personnel to change tip assemblies. Still another advantage of this version of tip assembly 30 is that since the tip assembly can be used to deliver irrigating fluid in two spray patterns, the need to keep two separate tip assemblies, that only differ by nozzle design, is eliminated.

Also, nozzle assembly 410 of this invention diffuses the discharged irrigation fluid after the fluid has already been discharged from the discharge tube 32. It does not impose a restriction on fluid flow while the irrigating fluid is in the discharge tube 32. Thus, nozzle assembly 410 of this invention, when employed to diffuse fluid flow, does not impose a pressure drop on the fluid as it is discharged which can adversely effect the efficiency of the pump 24.

The foregoing description has been directed to several preferred embodiments of the invention. It should be clear that the structure of the invention may differ from what has been described. For example, there is no requirement that all versions of the invention employ the described tip lock. Other versions of the invention may employ other tip locks and even other tip assemblies. Also, there is no requirement that handpiece 22 be manufactured out of two opposed shells. In some versions of the invention, the handpiece may consist of a single piece housing that is formed with a channel in which the drain tube 50 is fitted. In these, as well as other versions of the invention, it may be desirable to employ other means to secure the drain tube in the housing. For example, it may be desirable to employ an adhesive to bond the drain tube to a wall internal to the housing that forms the channel in which the drain tube is seated.

It should likewise be understood that not all versions of the handpiece of this invention may include pumps and complementary motors for providing the discharge force for the fluid pulses. In some versions of the invention, the fluid may actually be pumped from a pump that is separate from the handpiece. In these versions of the invention, supply tube 28 or some conduit connected to supply tube 28 may be connected directly to the discharge head of the handpiece.

Furthermore, in versions of the invention in which the on/off and speed control is employed, the trigger structure may be different from what has been described. In some versions of the invention, the trigger may be a press-button that is normally biased to hold the complementary wiper in the off state. Alternatively, the trigger may be a component that is integrally formed with the body handpiece. In these versions of the invention, the trigger may be a cantilever arm that is integrally molded as part of the body of the handpiece. This arm would be connected to the wiper so that movement of the arm would result in displacement of the wiper. In these versions of the invention, owing to the molding of the cantilever arm, when the arm is its normal, static state it would hold the wiper in off position. The application of manual force to deflect the arm would move the wiper to position in which the wiper would electrically connect the motor to the batteries or power pack.

Also, the tip assembly may be structurally different from what has been described. For instance, in some version of the invention, discharge tube 32 may be provided with an outwardly extending ring that forms a seal with the spray shield 181 and suction tube 48 is formed with an annular groove in which a complementary seal integral with the spray shield seats. It should further be recognized that some tip assemblies may not even have suction tubes. Alternative nozzles may also be provided. For example, the nozzle may be integrally formed with the discharge tube. Also, while the necks of the discharge tube and suction tube are shown as being separated from the bodies of these tubes by distinct steps, that need not always be the case.

Moreover, in some versions of the invention, it may be desirable to mount a slidable spray shield to the tip assembly. Typically, but not always, these tip assemblies will not include a suction tube. In these versions of the invention, the spray shield will move along the length of the discharge tube. An O-ring may be mounted in the portion of the spray shield seated around the discharge tube to prevent back leakage of irrigating fluid.

Also, it may be desirable to provide some sort of locking mechanism to hold the spray shield to the rest of the tip assembly. For example, the opposed surfaces of the spray shield 181 that form slit 183 can be provided with a complementary boss-in-bore that form a snap lock. Also, the channels 215 may not be required. In the place of the channels, small bores may be formed in the portion of the spray shield 181 that define discharge chamber 210. Furthermore different constructions of the adjustable nozzle are possible. In some nozzles constructed according to this invention, it may be possible to set the rotating spray head to an intermediate position in which it deflects only a fraction of the fluid stream discharged out of the fixed base of the nozzle.

Also, while one particular trigger assembly for regulating the potential of the drive signal applied to the motor 34 has been disclosed, it should be clear that others may be employed. Thus, in some versions of the invention, resistor 68 may be eliminated. In these versions of the invention, the number of different speeds at which the irrigator would operate would be a function of the number of separate power conductors tied from the battery pack or rechargeable power pack to the handpiece. If, for example, there were three power conductors, then the irrigator would only operate at three speeds. In the power pack employed with these versions of the invention, the necessary modifications would have to be made to its internal regulator to determine through which of the three conductors there was current flow. It would similarly be necessary to design the speed regulator to ensure that it could cause three different PWM drive signals to be produced.

Alternative constructions of the trigger assembly are also possible. The loop in the spring 66 may not always be necessary to define a pivot point for the spring. Still in other versions of the invention, other members may be employed as the wiper that provides contact at various positions along resistor 68 and with contact 70. In most versions of the invention, it is contemplated that the wiper be formed of material that, in addition to being conductive, is also flexible.

Also, some trigger locks may be designed to hold the trigger in intermediate positions in addition to the position required for high speed operation.

Figure 20:
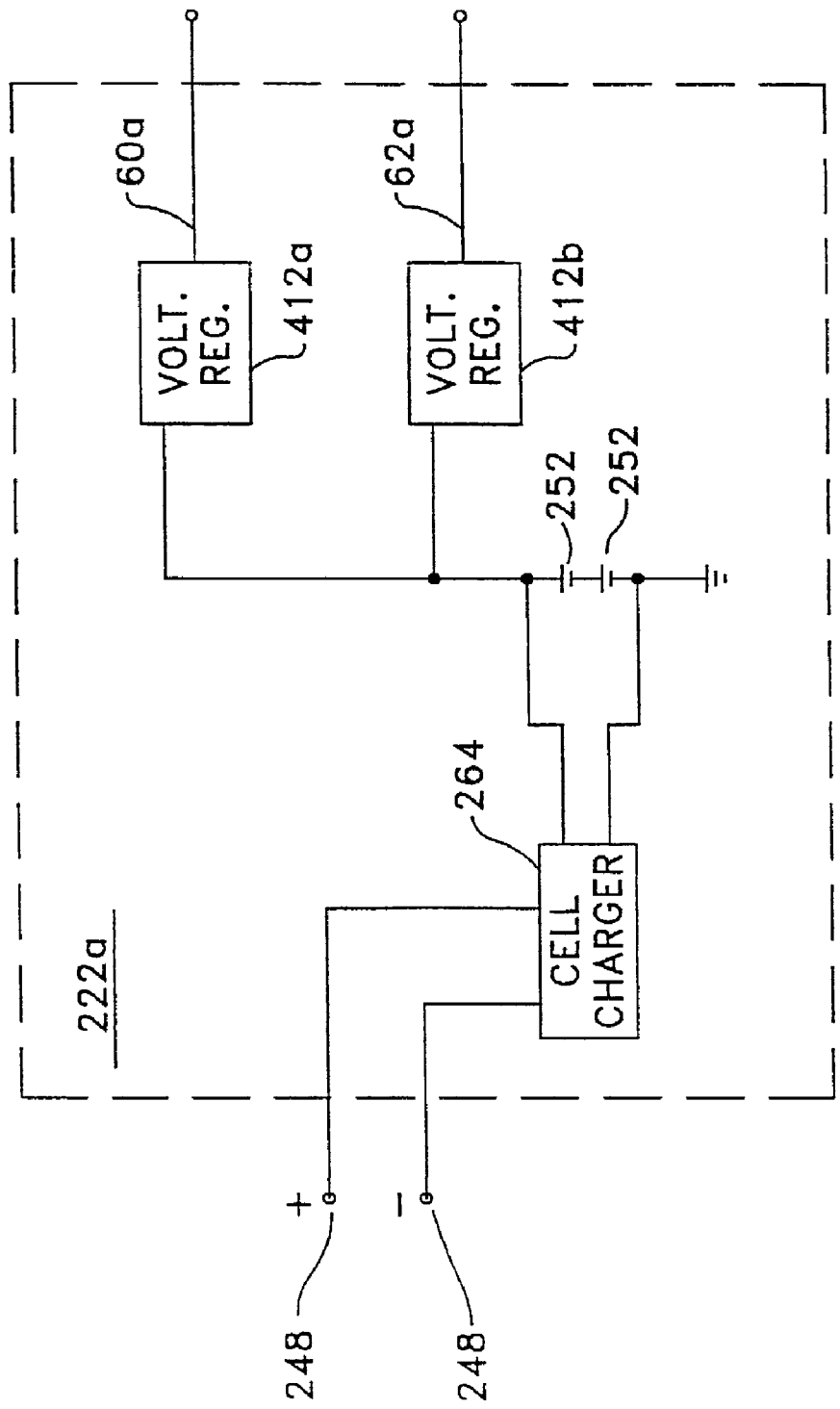
FIG. 20 is a block diagram of an alternative power pack of this invention.

It should similarly be recognized that the power pack may employ alternative circuitry for charging cells 252. For example, it may desirable to build an alternative power pack with a plug that allows it to be coupled to a conventional 120 VAC wall outlet. In these versions of the invention, the power pack may then incorporate a step-down transformer to lower the AC signal to a level at which it can be rectified. Likewise, alternative circuitry for ensuring that the cells 252 are uniformly discharged and/or are not excessively discharged may be employed. For example, as seen in FIG. 20, in some versions of the invention, it may be desirable to provide the power pack 222a with a number of different voltage regulators 412a and 412b to the power conductors 60a and 62, respectively, for providing drive signals of different potentials. Alternatively, the power conductors may be connected to a switchable voltage regulator. In this version of the invention, the voltage produced by the regulator would be based on the determination of which power conductor was serving as the conduit over which the drive signal was being applied to the handpiece 22a. Alternatively, zener diodes may be used to set the voltage of the drive signal applied to the handpiece 22a from the power pack 222.

Therefore, it is the object of the appended claims to cover all such modifications and variations as come within the true spirit and scope of the invention.

The embodiments of the invention in which an exclusive property or privilege is claimed are defined as follows:

1. A medical irrigator comprising:
   a handpiece;
   a discharge tube extending from said handpiece for receiving irrigating fluid, said discharge tube having a distal end with an opening through which irrigating fluid is discharged;
   a splash shield that extends forward beyond the distal end of said discharge tube, said splash shield being shaped to define a discharge chamber that has a first end adjacent the distal end of said discharge tube and a second end spaced forward of the discharge tube, said splash shield being shaped so that the second end is open, said discharge tube and said splash shield being collectively positioned and dimensioned so that irrigating fluid is discharged from the discharge tube opening into the first end of the discharge chamber towards the second end of the discharge chamber, and said splash shield is further formed to have an opening that extends from the discharge chamber, the opening being located between the first and second ends of the discharge chamber; and
   a suction conduit that extends from the opening in the splash shield discharge chamber.

2. The medical irrigator of claim 1, wherein said suction conduit is defined by:
   a suction tube that is attached to said handpiece or said discharge tube, said suction tube having a distal end with an opening, the distal end being connected to said splash shield; and
   a bore in said splash shield that extends from the opening in the discharge chamber towards the suction tube, the distal end opening of said suction tube being in fluid communication with the splash shield bore.

3. The medical irrigator of claim 2, wherein: said splash shield is removably attached to said discharge tube and to said suction tube.

4. The medical irrigator of claim 2, wherein a first seal is disposed between said discharge tube and said splash shield, and a second seal is disposed between said suction tube and said splash shield.

5. The medical irrigator of claim 1, wherein said splash shield is formed so that the opening in the discharge chamber is located closer to the second end of the discharge chamber than the first end of the discharge chamber.

6. The medical irrigator of claim 1, wherein said splash shield is formed so as to have at least one secondary opening into the discharge chamber that extends to the ambient environment.

7. The medical irrigator of claim 6, wherein said splash shield has an outwardly directed lip that extends around the second end of the discharge chamber and said lip is formed with at least one groove that extends between the ambient environment and the discharge chamber, the at least one groove being the at least one secondary opening.

8. The medical irrigator of claim 6, wherein said splash shield is formed so that the at least one secondary opening is located opposite the opening in said discharge chamber from which said suction conduit extends.

9. The medical irrigator of claim 1, wherein: said splash shield is removably attached to said discharge tube.

10. The medical irrigator of claim 9, wherein a seal extends around the distal end of said discharge tube between said discharge tube and said splash shield; said seal including a member attached to said splash shield that abuts an opposed surface of said discharge tube.

11. The medical irrigator of claim 1, wherein: a drain tube is mounted to said handpiece; and said suction conduit is connected to said drain tube.

12. The medical irrigator of claim 1, wherein said splash shield is shaped so that the first and second ends of the discharge chamber each has a width and the width of the second end of the discharge chamber is greater than the width of the first end of the discharge chamber.

13. The medical irrigator of claim 1, wherein a pump is disposed in said handpiece for forcing irrigating fluid therethrough, and said discharge tube is connected to said pump for receiving irrigating fluid therefrom.

14. A medical irrigator comprising:
   a handpiece;
   a discharge tube that extends from said handpiece for receiving irrigating fluid, said discharge tube having a distal end with an opening through which irrigating fluid is discharged;
   a suction tube that extends forward from said handpiece, said suction tube having a distal end; and
   a splash shield formed of flexible material, said splash shield having a base that is disposed over the distal end of said discharge tube and a head that extends distally from said base, said splash shield head being shaped to define: an open ended discharge chamber for receiving the irrigating fluid discharged from said discharge tube; and an opening in the discharge chamber, said suction tube being connected to said splash shield and in fluid communication with the discharge chamber through the opening formed in the discharge chamber.

15. The medical irrigator of claim 14, wherein said splash shield is formed with a bore that extends proximally from the opening formed in the discharge chamber and the distal end of said suction tube is seated in a proximal end section of the bore.

16. The medical irrigator of claim 15, wherein said splash shield is removably attached to said discharge tube and said suction tube.

17. The medical irrigator of claim 14, wherein said splash shield is formed so that the opening into the discharge chamber is located closer to the open end of the discharge chamber than an opposed end of the discharge chamber into which irrigating fluid from said discharge tube is discharged.

18. The medical irrigator of claim 14, wherein said splash shield is formed to have at least one secondary opening extending through a sidewall of said head, said opening extending from the ambient environment to the discharge chamber.

19. The medical irrigator of claim 18, wherein said splash shield is formed to have an outwardly extending lip around the open end of the discharge chamber and said lip is formed with at least one groove, the at least one groove being the at least one secondary opening.

20. The medical irrigator of claim 18, wherein said splash shield is formed so that the at least one secondary opening is located opposite the opening formed in the discharge chamber to which said suction tube is connected.

21. The medical irrigator of claim 14, wherein: said splash shield is removably attached to said discharge tube and a seal extends between said discharge tube and said splash shield.

22. The medical irrigator of claim 21, wherein said seal comprises a member attached to said splash shield that abuts an adjacent surface of said discharge tube.

23. The medical irrigator of claim 14, wherein said splash shield is formed so that said discharge chamber has a width that increases as the discharge chamber extends distally from the base of said splash shield.

24. A medical irrigator comprising:
a handpiece;
a discharge tube extending from said handpiece, said discharge tube having a first end connected to said handpiece for receiving the irrigating fluid and a second end located forward of said handpiece, the second end having an opening through which irrigating fluid is discharged;
a suction tube connected to said handpiece and having a first end located adjacent said handpiece and a second end located forward of said handpiece; and
a splash shield formed of flexible material, said splash shield being connected to said discharge tube and said suction tube and being shaped to define:
an open-ended discharge chamber that is located forward of said discharge tube that is in fluid communication with the opening in the second end of said discharge tube;
a first bore, said suction tube being connected to said first bore; and
a first opening in the discharge chamber that is located forward of where the irrigating fluid is introduced into the discharge chamber from said discharge tube, wherein the first bore is connected to the discharge chamber through the first opening.

25. The medical irrigator of claim 24, wherein: said splash shield is removably attached to said discharge tube and said suction tube.

26. The medical irrigator of claim 25, wherein said splash shield is further formed so as to have at least one second opening that extends from the ambient environment, through said splash shield, and into the discharge chamber.

27. The medical irrigator of claim 26, wherein: said splash shield is formed to have a lip around the open end of said discharge chamber; and said lip is formed to have at least one groove that extends from the ambient environment into the discharge chamber, the at least one groove being the at least one second opening into said discharge chamber.

28. The medical irrigator of claim 24, wherein:
said discharge tube and said suction tube are connected together as a single unit;
said discharge tube and said suction tube are removably attached to said handpiece; and
said splash shield is removably attached to said discharge tube and said suction tube.

29. The medical irrigator of claim 24, wherein said splash shield is formed so that the discharge chamber has a narrow width adjacent where said discharge tube is connected to the discharge chamber and a wide width at the open end of the discharge chamber.

30. The medical irrigator of claim 24, wherein a first seal extends between said discharge tube and said splash shield, and a second seal extends between said suction tube and said splash shield.

31. The medical irrigator of claim 30, wherein said first seal and said second seal are separate components.

32. The medical irrigator of claim 30, wherein said first seal is formed with said splash shield.

33. The medical irrigator of claim 30, wherein: said splash shield is formed with a second bore; the second end of said discharge tube is seated in the second bore of said splash shield; and said first seal is formed by a portion of said splash shield that extends into the splash shield second bore.

34. The medical irrigator of claim 30, wherein said second seal is formed by a portion of said suction tube that abuts an adjacent surface of said splash shield.

35. A medical irrigator, said irrigator comprising:
a handpiece,
a discharge tube extending from said handpiece for receiving irrigating fluid, said discharge tube having a distal end with an opening through which the irrigating fluid is discharged and defining a groove which extends circumferentially around said distal end; and
a splash shield formed of flexible material, said splash shield having a base that is removably attached to the distal end of said discharge tube and a head located forward of said base, said head defining an open ended discharge chamber into which the irrigating fluid from the discharge tube opening is discharged; and
a seal attached to said splash shield and extending between said distal end of said discharge tube and said splash shield base, said seal seating in the grove formed in said discharge tube.

36. The medical irrigator of claim 35, wherein:
a suction tube extends from said handpiece, said suction tube having a distal end with an opening;
said splash shield is removably seated over the distal end of said suction tube and is formed with an opening that establishes a fluid communication path between the discharge chamber and the opening in the distal end of said suction tube; and said seal between said discharge tube and said splash shield base is a first seal, and a second seal is located between the distal end of said suction tube and said splash shield.

37. The medical irrigator of claim 36, wherein said second seal is a member attached to said suction tube that bears against an opposed surface of said splash shield.

38. The medical irrigator of claim 37, wherein said splash shield is shaped so that the discharge chamber has a narrow width adjacent said splash shield base and a wide width adjacent the open end of said discharge chamber.

39. The medical irrigator of claim 35, wherein:

a suction tube is attached to said discharge tube so that said discharge tube and said suction tube form a single unit, said suction tube having a proximal end coupled to said handpiece and a distal end adjacent the distal end of said discharge tube;

said discharge tube and said suction tube are removably attached to said handpiece;

said splash shield base is removably attached to the distal end of said suction tube and is formed with a bore that extends from said suction tube to the discharge chamber; and said seal between said discharge tube and said splash shield base is a first seal and a second seal separate from said first seal extends between said distal end of said suction tube and said splash shield base.

* * * * *